United States Patent [19]
Snodgrass et al.

[11] Patent Number: 5,912,123
[45] Date of Patent: Jun. 15, 1999

[54] DETECTION OF THE LEPTIN RECEPTOR IN REPRODUCTIVE ORGANS AND METHODS FOR REGULATING REPRODUCTIVE BIOLOGY

[75] Inventors: H. Ralph Snodgrass, Powell; Joseph Cioffi, New Albany; Thomas Joel Zupancic, Worthington; Alan Wayne Shafer, Lancaster, all of Ohio

[73] Assignee: Progenitor, Inc., Menlo Park, Calif.

[21] Appl. No.: 08/640,389

[22] Filed: Apr. 29, 1996

Related U.S. Application Data

[63] Continuation-in-part of application No. 08/355,888, Dec. 14, 1994, Pat. No. 5,763,211, which is a continuation-in-part of application No. 08/306,231, Sep. 14, 1994, Pat. No. 5,643,748.

[51] Int. Cl.$^6$ .......................... C07H 21/04; C12P 19/34; C12Q 1/68
[52] U.S. Cl. .......................... 435/6; 435/91.2; 536/23.1; 536/24.31; 536/24.33; 935/77; 935/78
[58] Field of Search .................................. 435/6, 4, 91.1, 435/91.2; 536/23.1, 24.3, 24.33; 935/77, 78

[56] References Cited

FOREIGN PATENT DOCUMENTS

| | | |
|---|---|---|
| 0 409 607 A2 | 1/1991 | European Pat. Off. . |
| 0 521 156 A1 | 1/1993 | European Pat. Off. . |
| WO 88/02757 | 4/1988 | WIPO . |
| WO 93/10151 | 5/1993 | WIPO . |

OTHER PUBLICATIONS

Baringa, 1996, "Obesity: Leptin Receptor Weights In," *Science* 271:29.
Tartaglia et al., 1995, "Identification and Expression Cloning of a Leptin Receptor, OB–R," *Cell* 83:1263–1271.
Chehab et al., 1996, "Correction of the Sterility Defect in Homozygous Obese Female Mice by Treatment With the Human Recombinant Leptin," *Nature Genetics* 12:318–320.
Pelleymounter et al., 1995, "Effects of the obese Gene Product on Body Weight Regulation in ob/ob Mice," *Science* 269:540–549.
Beckmann et al., 1994, "Molecular characterization of a family of ligands for eph–related tyrosine kinase receptors," *The EMBO Journal* 13(16):3757–3762.
Miyajima et al., 1993, "Receptors for Granulocyte–Macrophage Colony–Stimulating Factor, Inteleukin–3, and Interleukin–5," *Blood* 82(7):1960–1974.
Saito et al., 1992, "Molecular Cloning of a Murine IL–6 Receptor–Associated Signal Transducer, gp 130, and its Regulated Expression in Vivo," *J. Immunol.* 148(12):4066–4071.
Park et al., 1992, "Cloning of the low–affinity murine granulocyte–macrophage colony–stimulating factor receptor and reconstitution of a high–affinity receptor complex," *Proc. Natl. Acad. Sci. U.S.A.* 89:4295–4299.
Miyajima et al., 1992, "Cytokine Receptors and Signal Transduction," *Ann. Rev. Immunol.* 10:295–331.
Truett et al., 1991, "Rat obesity gene fatty (fa) maps to chromosome 5: Evidence for homology with the mouse gene diabetes (db)," *Proc. Natl. Acad. Sci. U.S.A.* 88:7806–7809.
Larsen et al., 1990, "Expression Cloning of a Human Granulocyte Colony–stimulating Factor Receptor: A Structural Mosaic of Hematopoietin Receptor, Immunoglobulin, and Fibronectin Domains," *J. Exp. Med.* 172:1559–1570.
Hibi et al., 1990, "Molecular Cloning and Expression of a IL–6 Signal Transducer, gp130," *Cell* 63:1149–1157.
Hayashida et al., 1990, "Molecular cloning of a second subunit of the receptor for human granulocyte–macrophage colony–stimulating factor (GM–CSF): Reconstitution of a high–affinity GM–CSF receptor," *Proc. Natl. Acad. Sci. U.S.A.* 87:9655–9659.
Harada et al., 1990, "Expression Cloning of a cDNA Encoding the Murine Interleukin 4 Receptor Based on Ligand Binding," *Proc. Natl. Acad. Sci. U.S.A.* 87:857–861.
Gorman et al., 1990, "Cloning and Expression of a Gene Encoding an Interleukin 3 receptor–Like Protein: Identification of Another Member of the Cytokine Receptor Gene Family," *Proc. Natl. Acad. Sci. U.S.A.* 87:5459–5463.
Fukunaga et al., 1990, "Expression Cloning of a Receptor for Murine Granulocyte Colony–Stimulating Factor," *Cell* 61:341–350.
Cosman et al., 1990, "A new Cytokine Receptor Superfamily," *TIBS* 15:265–269.
Bazan, 1990, "Structural Design and Molecular Evolution of a Cytokine Receptor Superfamily," *Proc. Natl. Acad. Sci. U.S.A.* 87:6934–6938.
Bahary et al., 1990, "Molecular Mapping of the Mouse db Mutation," *Proc. Natl. Acad. Sci. U.S.A.* 87:8642–8646.
Mosley et al., 1989, "The Murine Interleukin–4 Receptor: Molecular Cloning and Characterization of Secreted and Membrane Bound Forms," *Cell* 59:335–348.
Gearing et al., 1989, "Expression cloning of a receptor for human granulocyte–macrophage colony–stimulating factor," *The EMBO Journal* 8(12):3667–3676.
Yamasaki et al., 1988, "Cloning and Expression of the Human Interleukin–6 (BSF–2/IFN/62 2) Receptor," *Science* 241:825–828.
Gearing et al., 1987, "Molecular Cloning and Expression of cDNA Encoding a Murine Myeloid Leukaemia Inhibitory Factor (LIF)," *The EMBO Journal* 6:3995–4002.

*Primary Examiner*—Stephanie W. Zitomer
*Attorney, Agent, or Firm*—Pennie & Edmonds LLP

[57] ABSTRACT

The present invention relates to variant forms of the receptor for the obese gene product. In particular, the invention relates to methods of detecting receptor variants in the reproductive organs for the diagnosis of the cause of infertility. In addition, it relates to methods of inhibiting or down-regulating expression of defective variants in cells to augment their responsiveness to regulation by leptin as well as methods of using compounds to directly activate signal transduction pathways associated with this ligand-receptor system to improve fertility.

48 Claims, 11 Drawing Sheets

```
        9                18                27                36                45            54
GCG CGC GCG ACG CAG GTG CCC GAG CCC CGG CCC GCG CCC ATC TCT GCC TTC GGT
 A   R   A   T   Q   V   P   E   P   R   P   A   P   I   S   A   F   G 63                72                90                99           108
CGA GTT GGA CCC CCG GAT CAA GGT GTA CTT CTC TGA AGT AAG ATG ATT TGT CAA
 R   V   G   P   P   D   Q   G   V   L   L   *   S   K   M   I   C   Q 117               126               135       144           153           162
AAA TTC TGT GTG GTT TTG TTA CAT TGG GAA TTT ATT TAT GTG ATA ACT GCG TTT
 K   F   C   V   V   L   L   H   W   E   F   I   Y   V   I   T   A   F 171           180           189           198           207           216
AAC TTG TCA TAT CCA ATT ACT CCT TGG AGA TTT AAG TTG TCT TGC ATG CCA CCA
 N   L   S   Y   P   I   T   P   W   R   F   K   L   S   C   M   P   P 225           234           243           252           261           270
AAT TCA ACC TAT GAC TAC TTC CTT TTG CCT GCT GGA CTC TCA AAG AAT ACT TCA
 N   S   T   Y   D   Y   F   L   L   P   A   G   L   S   K   N   T   S 279           288           297           306           315           324
AAT TCG AAT GGA CAT TAT GAG ACA GCT GTT GAA CCT AAG TTT AAT TCA AGT GGT
 N   S   N   G   H   Y   E   T   A   V   E   P   K   F   N   S   S   G 333           342           351           360           369           378
ACT CAC TTT TCT AAC TTA TCC AAA GCA ACT TTC CAC TGT TGC TTT CGG AGT GAG
 T   H   F   S   N   L   S   K   A   T   F   H   C   C   F   R   S   E 387           396           405           414           423           432
CAA GAT AGA AAC TGC TCC TTA TGT GCA GAC AAC ATT GAA GGA AGG ACA TTT GTT
 Q   D   R   N   C   S   L   C   A   D   N   I   E   G   R   T   F   V 441           450           459           468           477           486
TCA ACA GTA AAT TCT TTA GTT TTT CAA CAA ATA GAT GCA AAC TGG AAC ATA CAG
 S   T   V   N   S   L   V   F   Q   Q   I   D   A   N   W   N   I   Q 495           504           513           522           531           540
TGC TGG CTA AAA GGA GAC TTA AAA TTA TTC ATC TGT TAT GTG GAG TCA TTA TTT
 C   W   L   K   G   D   L   K   L   F   I   C   Y   V   E   S   L   F 549           558           567           576           585           594
AAG AAT CTA TTC AGG AAT TAT AAC TAT AAG GTC CAT CTT TTA TAT GTT CTG CCT
 K   N   L   F   R   N   Y   N   Y   K   V   H   L   L   Y   V   L   P 603           612           621           630           639           648
GAA GTG TTA GAA GAT TCA CCT CTG GTT CCC CAA AAA GGC AGT TTT CAG ATG GTT
 E   V   L   E   D   S   P   L   V   P   Q   K   G   S   F   Q   M   V
```

FIG.1A

```
CAC TGC  657  TGC AGT  666  CAT GAA  675  TGT GAA  684  CTT GTG  693  GTG CCA  702
    AAT          GTT          TGT          TGT          CCT          ACA
 H   C   N   C   S   V   H   E   C   C   E   C   L   V   P   V   P   T

GCC AAA  711  AAC GAC  720  CTC CTT  729  TGT TTG  738  ATC ACA  747  GGT GGA  756
    CTC          ACT          ATG          AAA          TCT          GTA
 A   K   L   N   D   T   L   L   M   C   L   K   I   T   S   G   G   V

ATT TTC  765  TCA CCT  774  ATG TCA  783  CAG CCC  792  AAT ATG  801  AAG CCT  810
    CGG          CTA          GTT          ATA          GTG          GAT
 I   F   R   S   P   L   M   S   V   Q   P   I   N   M   V   K   P   D

CCA CCA  819  GGT TTG  828  ATG GAA  837  ACA GAT  846  GGT AAT  855  AAG ATT  864
    TTA          CAT          ATC          GAT          TTA          TCT
 P   P   L   G   L   H   M   E   I   T   D   D   G   N   L   K   I   S

TGG TCC  873  CCA CCA  882  GTA CCA  891  CCA CTT  900  TAT CAA  909  AAA TAT  918
    AGC          TTG          TTT          CAA          GTG          TCA
 W   S   S   P   P   L   V   P   F   P   L   Q   Y   Q   V   K   Y   S

GAG AAT  927  ACA ACA  936  ATC AGA  945  GCT GAC  954  ATT GTC  963  GCT ACA  972
    TCT          GTT          GAA          AAG          TCA          TCC
 E   N   S   T   T   V   I   R   E   A   D   K   I   V   S   A   T   S

CTG CTA  981  GAC AGT  990  CTT CCT  999  TCT TCG 1008  GAG GTT 1017  GTG AGG 1026
    GTA          ATA          GGG          TAT          CAG          GGC
 L   L   V   D   S   I   L   P   G   S   S   Y   E   V   Q   V   R   G

AAG AGA 1035  GAT GGC 1044  GGA ATC 1053  AGT GAC 1062  AGT ACT 1071  CGT GTC 1080
    CTG          CCA          TGG          TGG          CCT          TTT
 K   R   L   D   G   P   G   I   W   S   D   W   S   T   P   R   V   F

ACC ACA 1089  GAT GTC 1098  TAC TTT 1107  CCT AAA 1116  CTG ACA 1125  GTT GGG 1134
    CAA          ATA          CCA          ATT          AGT          TCT
 T   T   Q   D   V   I   Y   F   P   P   K   I   L   T   S   V   G   S

AAT GTT 1143  TTT CAC 1152  ATC TAT 1161  AAG AAG 1170  AAG ATT 1179  CCC TCA 1188
    TCT          TGC          AAG          GAA AAC      GTT          AAA
 N   V   S   F   H   C   I   Y   K   K   E   N   K   I   V   P   S   K

GAG ATT 1197  TGG TGG 1206  AAT TTA 1215  GAG AAA 1224  CCT CAA 1233  CAG TAT 1242
    GTT          ATG          GCT          ATT          AGC          GAT
 E   I   V   W   W   M   N   L   A   E   K   I   P   Q   S   Q   Y   D

GTT GTG 1251  GAT CAT 1260  AGC AAA 1269  ACT TTT 1278  AAT CTG 1287  GAA ACC 1296
    AGT          GTT          GTT          TTC          AAT          AAA
 V   V   S   D   H   V   S   K   V   T   F   F   N   L   N   E   T   K

CCT CGA 1305  AAG TTT 1314  TAT GAT 1323  GTG TAC 1332  TGC AAT 1341  CAT GAA 1350
    GGA          ACC          GCA          TGC          GAA          TGC
 P   R   G   K   F   T   Y   D   A   V   Y   C   C   N   E   H   E   C
```

FIG.1B

```
CAT CAT CGC TAT GCT GAA TTA TAT GTG ATT GAT GTC AAT ATC AAT ATC TCA TGT
     1359         1368        1377        1386        1395        1404
 H   H   R   Y   A   E   L   Y   V   I   D   V   N   I   N   I   S   C

GAA ACT GAT GGG TAC TTA ACT AAA ATG ACT TGC AGA TGG TCA ACC AGT ACA ATC
     1413        1422        1431        1440        1449        1458
 E   T   D   G   Y   L   T   K   M   T   C   R   W   S   T   S   T   I

CAG TCA CTT GCG GAA AGC ACT TTG CAA TTG AGG TAT CAT AGG AGC AGC CTT TAC
     1467        1476        1485        1494        1503        1512
 Q   S   L   A   E   S   T   L   Q   L   R   Y   H   R   S   S   L   Y

TGT TCT GAT ATT CCA TCT ATT CAT CCC ATA TCT GAG CCC AAA GAT TGC TAT TTG
     1521        1530        1539        1548        1557        1566
 C   S   D   I   P   S   I   H   P   I   S   E   P   K   D   C   Y   L

CAG AGT GAT GGT TTT TAT GAA TGC ATT TTC CAG CCA ATC TTC CTA TTA TCT GGC
     1575        1584        1593        1602        1611        1620
 Q   S   D   G   F   Y   E   C   I   F   Q   P   I   F   L   L   S   G

TAC ACA ATG TGG ATT AGG ATC AAT CAC TCT CTA GGT TCA CTT GAC TCT CCA CCA
     1629        1638        1647        1656        1665        1674
 Y   T   M   W   I   R   I   N   H   S   L   G   S   L   D   S   P   P

ACA TGT GTC CTT CCT GAT TCT GTG GTG AAG CCA CTG CCT CCA TCC AGT GTG AAA
     1683        1692        1701        1710        1719        1728
 T   C   V   L   P   D   S   V   V   K   P   L   P   P   S   S   V   K

GCA GAA ATT ACT ATA AAC ATT GGA TTA TTG AAA ATA TCT TGG GAA AAG CCA GTC
     1737        1746        1755        1764        1773        1782
 A   E   I   T   I   N   I   G   L   L   K   I   S   W   E   K   P   V

TTT CCA GAG AAT AAC CTT CAA TTC CAG ATT CGC TAT GGT TTA AGT GGA AAA GAA
     1791        1800        1809        1818        1827        1836
 F   P   E   N   N   L   Q   F   Q   I   R   Y   G   L   S   G   K   E

GTA CAA TGG AAG ATG TAT GAG GTT TAT GAT GCA AAA TCA AAA TCT GTC AGT CTC
     1845        1854        1863        1872        1881        1890
 V   Q   W   K   M   Y   E   V   Y   D   A   K   S   K   S   V   S   L

CCA GTT CCA GAC TTG TGT GCA GTC TAT GCT GTT CAG GTG CGC TGT AAG AGG CTA
     1899        1908        1917        1926        1935        1944
 P   V   P   D   L   C   A   V   Y   A   V   Q   V   R   C   K   R   L

GAT GGA CTG GGA TAT TGG AGT AAT TGG AGC AAT CCA GCC TAC ACA GTT GTC ATG
     1953        1962        1971        1980        1989        1998
 D   G   L   G   Y   W   S   N   W   S   N   P   A   Y   T   V   V   M

GAT ATA AAA GTT CCT ATG AGA GGA CCT GAA TTT TGG AGA ATA ATT AAT GGA GAT
     2007        2016        2025        2034        2043        2052
 D   I   K   V   P   M   R   G   P   E   F   W   R   I   I   N   G   D
```

FIG.1C

```
ACT ATG AAA AAG GAG AAA AAT GTC ACT TTA CTT TGG AAG CCC CTG ATG AAA AAT
     2061      2070      2079      2088      2097      2106
 T   M   K   K   E   K   N   V   T   L   L   W   K   P   L   M   K   N

GAC TCA TTG TGC AGT GTT CAG AGA TAT GTG ATA AAC CAT CAT ACT TCC TGC AAT
         2115      2124      2133      2142      2151      2160
 D   S   L   C   S   V   Q   R   Y   V   I   N   H   H   T   S   C   N

GGA ACA TGG TCA GAA GAT GTG GGA AAT CAC ACG AAA TTC ACT TTC CTG TGG ACA
         2169      2178      2187      2196      2205      2214
 G   T   W   S   E   D   V   G   N   H   T   K   F   T   F   L   W   T

GAG CAA GCA CAT ACT GTT ACG GTT CTG GCC ATC AAT TCA ATT GGT GCT TCT GTT
         2223      2232      2241      2250      2259      2268
 E   Q   A   H   T   V   T   V   L   A   I   N   S   I   G   A   S   V

GCA AAT TTT AAT TTA ACC TTT TCA TGG CCT ATG AGC AAA GTA AAT ATC GTG CAG
         2277      2286      2295      2304      2313      2322
 A   N   F   N   L   T   F   S   W   P   M   S   K   V   N   I   V   Q

TCA CTC AGT GCT TAT CCT TTA AAC AGC AGT TGT GTG ATT GTT TCC TGG ATA CTA
         2331      2340      2349      2358      2367      2376
 S   L   S   A   Y   P   L   N   S   S   C   V   I   V   S   W   I   L

TCA CCC AGT GAT TAC AAG CTA ATG TAT TTT ATT ATT GAG TGG AAA AAT CTT AAT
         2385      2394      2403      2412      2421      2430
 S   P   S   D   Y   K   L   M   Y   F   I   I   E   W   K   N   L   N

GAA GAT GGT GAA ATA AAA TGG CTT AGA ATC TCT TCA TCT GTT AAG AAG TAT TAT
         2439      2448      2457      2466      2475      2484
 E   D   G   E   I   K   W   L   R   I   S   S   S   V   K   K   Y   Y

ATC CAT GAT CAT TTT ATC CCC ATT GAG AAG TAC CAG TTC AGT CTT TAC CCA ATA
         2493      2502      2511      2520      2529      2538
 I   H   D   H   F   I   P   I   E   K   Y   Q   F   S   L   Y   P   I

TTT ATG GAA GGA GTG GGA AAA CCA AAG ATA ATT AAT AGT TTC ACT CAA GAT GAT
         2547      2556      2565      2574      2583      2592
 F   M   E   G   V   G   K   P   K   I   I   N   S   F   T   Q   D   D

ATT GAA AAA CAC CAG AGT GAT GCA GGT TTA TAT GTA ATT GTG CCA GTA ATT ATT
         2601      2610      2619      2628      2637      2646
 I   E   K   H   Q   S   D   A   G   L   Y   V   I   V   P   V   I   I

TCC TCT TCC ATC TTA TTG CTT GGA ACA TTA TTA ATA TCA CAC CAA AGA ATG AAA
         2655      2664      2673      2682      2691      2700
 S   S   S   I   L   L   L   G   T   L   L   I   S   H   Q   R   M   K

AAG CTA TTT TGG GAA GAT GTT CCG AAC CCC AAG AAT TGT TCC TGG GCA CAA GGA
         2709      2718      2727      2736      2745      2754
 K   L   F   W   E   D   V   P   N   P   K   N   C   S   W   A   Q   G
```

FIG.1D

```
     2763          2772          2781          2790          2799          2808
CTT AAT TTT CAG AAG ATG CTT GAA GGC AGC ATG TTC GTT AAG AGT CAT CAC CAC
 L   N   F   Q   K   M   L   E   G   S   M   F   V   K   S   H   H   H 2817          2826          2835          2844          2853          2862
TCC CTA ATC TCA AGT ACC CAG GGA CAC AAA CAC TGC GGA AGG CCA CAG GGT CCT
 S   L   I   S   S   T   Q   G   H   K   H   C   G   R   P   Q   G   P 2871          2880          2889          2898          2907          2916
CTG CAT AGG AAA ACC AGA GAC CTT TGT TCA CTT GTT TAT CTG CTG ACC CTC CCT
 L   H   R   K   T   R   D   L   C   S   L   V   Y   L   L   T   L   P 2925          2934          2943          2952          2961          2970
CCA CTA TTG TCC TAT GAC CCT GCC AAA TCC CCC TCT GTG AGA AAC ACC CAA GAA
 P   L   L   S   Y   D   P   A   K   S   P   S   V   R   N   T   Q   E 2979          2988
TGA TCA ATA AAA AAA AAA AAA 3'
 *   S   I   K   K   K   K
```

FIG.1E

```
              2760       2770       2780       2790       2800
Form 1 2751 AGGACTTAAT TTTCAGAAGA TGCTTGAAGG CAGCATGTTC GTTAAGAGTC  2800
     2 2751 AGGACTTAAT TTTCAGAAGA AAATGCCTGG CACAAAGGAA CTACTGGGTG  2800
     3 2751 AGGACTTAAT TTTCAGAAGA GAACGGACAT TCTTTGAAGT CTAATCATGA  2800

2810       2820       2830       2840       2850
Form 1 2801 ATCACCACTC CCTAATCTCA AGTACCCAGG GACACAAACA CTGCGGAAGG  2850
     2 2801 GAGGTTGGTT GACTTAGGAA ATGCTTGTGA AGCTACGTCC TACCTCGTGC  2850
     3 2801 TCACTACAGA TGAACCCAAT GTGCCAACTT CCCAACAGTC TATAGAGTAT  2850

2860       2870       2880       2890       2900
Form 1 2851 CCACAGGGTC CTCTGCATAG GAAAACCAGA GACCTTTGTT CACTTGTTTA  2900
     2 2851 GCACCTGCTC TCCCTGAGGT GTGCACAATG ..........  ..........  2900
     3 2851 TAGAAGATTT TTACATTCTG AAGAAGG...  ..........  ..........  2900

2910       2920       2930       2940       2950
Form 1 2901 TCTGCTGACC CTCCCTCCAC TATTGTCCTA TGACCCTGCC AAATCCCCCT  2950
     2 2901 ..........  ..........  ..........  ..........  ..........  2950
     3 2901 ..........  ..........  ..........  ..........  ..........  2950

2960       2970       2980       2990       3000
Form 1 2951 CTGTGAGAAA CACCCAAGAA TGATCAATAA AAAAAAAAAA A.........  3000
     2 2951 ..........  ..........  ..........  ..........  ..........  3000
     3 2951 ..........  ..........  ..........  ..........  ..........  3000
```

FIG.2

```
          10         20         30         40         50
HuB1.219_1   1 MICQKFCVVL LHWEFIYVIT AFNLSYPITP WRFKLSCMPP NSTYDYFLLP  50
HuB1.219_2   1 MICQKFCVVL LHWEFLYVIT AFNLSYPITP WRFKLSCMPP NSTYDYFLLP  50
HuB1.219_3   1 MICQKFCVVL LHWEFIYVIT AFNLSYPITP WRFKLSCMPP NSTYDYFLLP  50
HuOBR        1 MICQKFCVVL LHWEFIYVIT AFNLSYPITP WRFKLSCMPP NSTYDYFLLP  50
MuOBR        1 MMCQKFYVVL LHWEFLYVIA ALNLAYPISP WRFKLFCGPP NTTDDSFLSP  50

60         70         80         90        100
HuB1.219_1  51 AGLSKNTSNS NGHYETAVEP KFNSSGTHFS NLSKATFHCC FRSEQDRNCS 100
HuB1.219_2  51 AGLSKNTSNS NGHYETAVEP KFNSSGTHFS NLSKATFHCC FRSEQDRNCS 100
HuB1.219_3  51 AGLSKNTSNS NGHYETAVEP KFNSSGTHFS NLSKATFHCC FRSEQDRNCS 100
HuOBR       51 AGLSKNTSNS NGHYETAVEP KFNSSGTHFS NLSKTTFHCC FRSEQDRNCS 100
MuOBR       51 AGAPNNASAL KGASEAIVEA KFNSSGIYVP ELSKTVFHCC FGNEQGQNCS 100

110        120        130        140        150
HuB1.219_1 101 LCADNIEGRT FVSTVNSLVF QQIDANWNIQ CWLKGDLKLF ICYVESLFKN 150
HuB1.219_2 101 LCADNIEGRT FVSTVNSLVF QQIDANWNIQ CWLKGDLKLF ICYVESLFKN 150
HuB1.219_3 101 LCADNIEGRT FVSTVNSLVF QQIDANWNIQ CWLKGDLKLF ICYVESLFKN 150
HuOBR      101 LCADNIEGKT FVSTVNSLVF QQIDANWNIQ CWLKGDLKLF ICYVESLFKN 150
MuOBR      101 ALTDNIEGKT LASMVKASVF RQLGVNWDIE CWMKGDLTLF IQHMEPLPKN 150

160        170        180        190        200
HuB1.219_1 151 LFRNYNYKVH LLYVLPEVLE DSPLVPQKGS FQMVHCNCSV HECCECLVPV 200
HuB1.219_2 151 LFRNYNYKVH LLYVLPEVLE DSPLVPQKGS FQMVHCNCSV HECCECLVPV 200
HuB1.219_3 151 LFRNYNYKVH LLYVLPEVLE DSPLVPQKGS FQMVHCNCSV HECCECLVPV 200
HuOBR      151 LFRNYNYKVH LLYVLPEVLE DSPLVPQKGS FQMVHCNCSV HECCECLVPV 200
MuOBR      151 PFKNYDSKVH LLYDLPEVID DSPLPPLKDS FQTVQCNCSL RGCEGHVPV  200

210        220        230        240        250
HuB1.219_1 201 PTAKLNDTLL MCLKITSGGV IFRSPLMSVQ PINMVKPDPP LGLHMEITDD 250
HuB1.219_2 201 PTAKLNDTLL MCLKITSGGV IFRSPLMSVQ PINMVKPDPP LGLHMEITDD 250
HuB1.219_3 201 PTAKLNDTLL MCLKITSGGV IFRSPLMSVQ PINMVKPDPP LGLHMEITDD 250
HuOBR      201 PTAKLNDTLL MCLKITSGGV IFQSPLMSVQ PINMVKPDPP LGLHMEITDD 250
MuOBR      201 PRAKLNYALL MYLEITSAGV SFQSPLMSLQ PMLVWKPDPP LGLHMEVTDD 250

260        270        280        290        300
HuB1.219_1 251 GNLKISWSSP PLVPFPLQYQ VKYSENSTTV IREADKIVSA TSLLVDSILP 300
HuB1.219_2 251 GNLKISWSSP PLVPFPLQYQ VKYSENSTTV IREADKIVSA TSLLVDSILP 300
HuB1.219_3 251 GNLKISWSSP PLVPFPLQYQ VKYSENSTTV IREADKIVSA TSLLVDSILP 300
HuOBR      251 GNLKISWSSP PLVPFPLQYQ VKYSENSTTV IREADKIVSA TSLLVDSILP 300
MuOBR      251 GNLKISWDSQ TMAPFPLQYQ VKYLENSTIV REAAFEIVSA TSLLVDSVLP 300
```

FIG.3A

```
              310         320         330         340         350
HuB1.219_1 301 GSSYEVQVRG  KRLDGPGIWS  DWSTPRVFTT  QDVIYFPPKI  LTSVGSNVSF 350
HuB1.219_2 301 GSSYEVQVRG  KRLDGPGIWS  DWSTPRVFTT  QDVIYFPPKI  LTSVGSNVSF 350
HuB1.219_3 301 GSSYEVQVRG  KRLDGPGIWS  DWSTPRVFTT  QDVIYFPPKI  LTSVGSNVSF 350
HuOBR      301 GSSYEVQVRG  KRLDGPGIWS  DWSTPRVFTT  QDVIYFPPKI  LTSVGSNVSF 350
MuOBR      301 GSSYEVQVRS  KRLDGSGVWS  DWSSHQVFTT  QDVMYFPPKI  LTSVGSNASF 350

360         370         380         390         400
HuB1.219_1 351 HCIYKKENKI  VPSKEIVWWM  NLAEKIPQSQ  YDVVSDHVSK  VTFFNLNETK 400
HuB1.219_2 351 HCIYKKENKI  VPSKEIVWWM  NLAEKIPQSQ  YDVVSDHVSK  VTFFNLNETK 400
HuB1.219_3 351 HCIYKKENKI  VPSKEIVWWM  NLAEKIPQSQ  YDVVSDHVSK  VTFFNLNETK 400
HuOBR      351 HCIYKKENKI  VPSKEIVWWM  NLAEKIPQSQ  YDVVSDHVSK  VTFFNLNETK 400
MuOBR      351 HCIYKNENQI  ISSKQIVWWR  NLAEKIPETQ  YSIVSDRVSK  VTFSNLKATR 400

410         420         430         440         450
HuB1.219_1 401 PRGKFTYDAV  YCCNEHECHH  RYAELYVIDV  NINISCETDG  YLTKMTCRWS 450
HuB1.219_2 401 PRGKFTYDAV  YCCNEHECHH  RYAELYVIDV  NINISCETDG  YLTKMTCRWS 450
HuB1.219_3 401 PRGKFTYDAV  YCCNEHECHH  RYAELYVIDV  NINISCETDG  YLTKMTCRWS 450
HuOBR      401 PRGKFTYDAV  YCCNEHECHH  RYAELYVIDV  NINISCETDG  YLTKMTCRWS 450
MuOBR      401 PRGKFTYDAV  YCCNEQACHH  RYAELYVIDV  NINISCETDG  YLTKMTCRWS 450

460         470         480         490         500
HuB1.219_1 451 TSTIQSLAES  TLQLRYHRSS  LYCSDIPSIH  PISEPKDCYL  QSDGFYECIF 500
HuB1.219_2 451 TSTIQSLAES  TLQLRYHRSS  LYCSDIPSIH  PISEPKDCYL  QSDGFYECIF 500
HuB1.219_3 451 TSTIQSLAES  TLQLRYHRSS  LYCSDIPSIH  PISEPKDCYL  QSDGFYECIF 500
HuOBR      451 TSTIQSLAES  TLQLRYHRSS  LYCSDIPSIH  PISEPKDCYL  QSDGFYECIF 500
MuOBR      451 PSTIQSLVGS  TMQLRYHRRS  LYCPDSPSIH  PTSEPKNCVL  QRDGFYECVF 500

510         520         530         540         550
HuB1.219_1 501 QPIFLLSGYT  MWIRINHSLG  SLDSPPTCVL  PDSVVKPLPP  SSVKAEITIN 550
HuB1.219_2 501 QPIFLLSGYT  MWIRINHSLG  SLDSPPTCVL  PDSVVKPLPP  SSVKAEITIN 550
HuB1.219_3 501 QPIFLLSGYT  MWIRINHSLG  SLDSPPTCVL  PDSVVKPLPP  SSVKAEITIN 550
HuOBR      501 QPIFLLSGYT  MWIRINHSLG  SLDSPPTCVL  PDSVVKPLPP  SSVKAEITIN 550
MuOBR      501 QPIFLLSGYT  MWIRINHSLG  SLDSPPTCVL  PDSVVKPLPP  SNVKAEITMN 550

560         570         580         590         600
HuB1.219_1 551 IGLLKISWEK  PVFPENNLQF  QIRYGLSGKE  VQWKMYEVYD  AKSKSVSLPV 600
HuB1.219_2 551 IGLLKISWEK  PVFPENNLQF  QIRYGLSGKE  VQWKMYEVYD  AKSKSVSLPV 600
HuB1.219_3 551 IGLLKISWEK  PVFPENNLQF  QIRYGLSGKE  VQWKMYEVYD  AKSKSVSLPV 600
HuOBR      551 IGLLKISWEK  PVFPENNLQF  QIRYGLSGKE  VQWKMYEVYD  AKSKSVSLPV 600
MuOBR      551 TGLLKVSWEK  PVFPENNLQF  QIRYGLSGKE  IQWKTHEVFD  AKSKSASLLV 600
```

FIG.3B

```
              610        620        630        640        650
HuB1.219_1 601 PDLCAVYAVQ VRCKRLDGLG YWSNWSNPAY TVVMDIKVPM RGPEFWRIIN 650
HuB1.219_2 601 PDLCAVYAVQ VRCKRLDGLG YWSNWSNPAY TVVMDIKVPM RGPEFWRIIN 650
HuB1.219_3 601 PDLCAVYAVQ VRCKRLDGLG YWSNWSNPAY TVVMDIKVPM RGPEFWRIIN 650
HuOBR      601 PDLCAVYAVQ VRCKRLDGLG YWSNWSNPAY TVVMDIKVPM RGPEFWRIIN 650
MuOBR      601 SDLCAVYWVQ VRCRRLDGLG YWSNWSSPAY TLVMDVKVPM RGPEFWRKMD 650

660        670        680        690        700
HuB1.219_1 651 GDTMKKEKNV TLLWKPLMKN DSLCSVQRYV INHHTSCNGT WSEDVGNHTK 700
HuB1.219_2 651 GDTMKKEKNV TLLWKPLMKN DSLCSVQRYV INHHTSCNGT WSEDVGNHTK 700
HuB1.219_3 651 GDTMKKEKNV TLLWKPLMKN DSLCSVQRYV INHHTSCNGT WSEDVGNHTK 700
HuOBR      651 GDTMKKEKNV TLLWKPLMKN DSLCSVQRYV INHHTSCNGT WSEDVGNHTK 700
MuOBR      651 GDVTKKERNV TLLWKPLTKN DSLCSVRRYV VKHRTAHNGT WSEDVGNRTN 700

710        720        730        740        750
HuB1.219_1 701 FTFLWTEQAH TVTVLAINSI GASVANFNLT FSWPMSKVNI VQSLSAYPLN 750
HuB1.219_2 701 FTFLWTEQAH TVTVLAINSI GASVANFNLT FSWPMSKVNI VQSLSAYPLN 750
HuB1.219_3 701 FTFLWTEQAH TVTVLAINSI GASVANFNLT FSWPMSKVNI VQSLSAYPLN 750
HuOBR      701 FTFLWTEQAH TVTVLAINSI GASVANFNLT FSWPMSKVNI VQSLSAYPLN 750
MuOBR      701 LTFLWTEPAH TVTVLAVNSL GASLVNFNLT FSWPMSKVSA VESLSAYPLS 750

760        770        780        790        800
HuB1.219_1 751 SSCVIVSWIL SPSDYKLMYF IIEWKNLNED GEIKWLRISS SVKKYYIHDH 800
HuB1.219_2 751 SSCVIVSWIL SPSDYKLMYF IIEWKNLNED GEIKWLRISS SVKKYYIHDH 800
HuB1.219_3 751 SSCVIVSWIL SPSDYKLMYF IIEWKNLNED GEIKWLRISS SVKKYYIHDH 800
HuOBR      751 SSCVIVSWIL SPSDYKLMYF IIEWKNLNED GEIKWLRISS SVKKYYIHDH 800
MuOBR      751 SSCVILSWTL SPDDYSLLYL VIEWKILNED DGMKWLRIPS NVKKFYIHDN 800

810        820        830        840        850
HuB1.219_1 801 FIPIEKYQFS LYPIFMEGVG KPKIINSFTQ DDIEKHQSDA GLYVIVPVII 850
HuB1.219_2 801 FIPIEKYQFS LYPIFMEGVG KPKIINSFTQ DDIEKHQSDA GLYVIVPVII 850
HuB1.219_3 801 FIPIEKYQFS LYPIFMEGVG KPKIINSFTQ DDIEKHQSDA GLYVIVPVII 850
HuOBR      801 FIPIEKYQFS LYPIFMEGVG KPKIINSFTQ DDIEKHQSDA GLYVIVPVII 850
MuOBR      801 FIPIEKYQFS LYPVFMEGVG KPKINGFTK DALDKQQNDA GLYVIVPTII 850

860        870        880        890        900
HuB1.219_1 851 SSSILLLGTL LISHQRMKKL FWEDVPNPKN CSWAQGLNFQ KMLEGSMFVK 900
HuB1.219_2 851 SSSILLLGTL LISHQRMKKL FWEDVPNPKN CSWAQGLNFQ KKMPGTKELL 900
HuB1.219_3 851 SSSILLLGTL LISHQRMKKL FWEDVPNPKN CSWAQGLNFQ KRTDIL.... 900
HuOBR      851 SSSILLLGTL LISHQRMKKL FWEDVPNPKN CSWAQGLNFQ KPETFEHLFI 900
MuOBR      851 SSCVLLLGTL LISHQRMKKL FWDDVPNPKN CSWAQGLNFQ KRTDTL*... 900
```

FIG. 3C

```
                      910        920        930        940        950
HuB1.219_1  901 SHHSLISST QGHKHCGRPQ GPLHRKTRDL CSLVYLLTLP PLLSYDPAKS 950
HuB1.219_2  901 GGGWLT.... .......... .......... .......... ..........  950
HuB1.219_3  901 .......... .......... .......... .......... ..........  950
HuOBR       901 KHTASVTCGP LLLEPETISE DISVDTSWKN KDEMMPTLVV SLLSTTDLEK  950
MuOBR       901 .......... .......... .......... .......... ..........  950

960        970        980        990       1000
HuB1.219_1  951 PSVRNTQE.. .......... .......... .......... .......... 1000
HuB1.219_2  951 .......... .......... .......... .......... .......... 1000
HuB1.219_3  951 .......... .......... .......... .......... .......... 1000
HuOBR       951 GSVCISDQFN SVNFSEAEGT EVTYEAESQR QPFVKYATLI SNSKPSETGE 1000
MuOBR       951 .......... .......... .......... .......... .......... 1000

1010       1020       1030       1040       1050
HuB1.219.1 1001 .......... .......... .......... .......... .......... 1050
HuB1.219_2 1001 .......... .......... .......... .......... .......... 1050
HuB1.219_3 1001 .......... .......... .......... .......... .......... 1050
HuOBR      1001 EQGLINSSVT KCFSSKNSPL KDSFSNSSWE IEAQAFFILS DQHPNIISPH 1050
MuOBR      1001 .......... .......... .......... .......... .......... 1050

1060       1070       1080       1090       1100
HuB1.219_1 1051 .......... .......... .......... .......... .......... 1100
HuB1.219_2 1051 .......... .......... .......... .......... .......... 1100
HuB1.219_3 1051 .......... .......... .......... .......... .......... 1100
HuOBR      1051 LTFSEGLDEL LKLEGNFPEE NNDKKSIYYL GVTSIKKRES GVLLTDKSRV 1100
MuOBR      1051 .......... .......... .......... .......... .......... 1100

1110       1120       1130       1140       1150
HuB1.219_1 1101 .......... .......... .......... .......... .......... 1150
HuB1.219_2 1101 .......... .......... .......... .......... .......... 1150
HuB1.219_3 1101 .......... .......... .......... .......... .......... 1150
HuOBR      1101 SCPFPAPCLF TDIRVLQDSC SHFVENNINL GTSSKKTFAS YMPQFQTCST 1150
MuOBR      1101 .......... .......... .......... .......... .......... 1150

1160       1170       1180       1190       1200
HuB1.219_1 1151 .......... .......... .......... .......... .......... 1200
HuB1.219_2 1151 .......... .......... .......... .......... .......... 1200
HuB1.219_3 1151 .......... .......... .......... .......... .......... 1200
HuOBR      1151 QTHKIMENKM CDLTV*.... .......... .......... .......... 1200
MuOBR      1151 .......... .......... .......... .......... .......... 1200
```

DETECTION OF THE LEPTIN RECEPTOR IN REPRODUCTIVE ORGANS AND METHODS FOR REGULATING REPRODUCTIVE BIOLOGY

The present application is a continuation-in-part of U.S. patent application Ser. No. 08/355,888, filed Dec. 14, 1994 (U.S. Pat. No. 5,763,111), which is a continuation-in-part of U.S. patent application Ser. No. 08/306,231, filed Sep. 14, 1994 (U.S. Pat. No. 5,643,748), each of which is incorporated by reference herein in its entirety.

INTRODUCTION

The present invention relates to variant forms of the receptor for the obese gene product. In particular, the invention relates to methods of detecting receptor variants in the reproductive organs for the diagnosis of the cause of infertility. In addition, it relates to methods of inhibiting or down-regulating expression of defective variants in cells to augment their responsiveness to regulation by leptin as well as methods of using compounds to directly activate signal transduction pathways associated with this ligand-receptor system to improve fertility.

BACKGROUND OF THE INVENTION

Infertility is a major clinical problem in Western societies. A number of contributing factors have been identified for infertility, which include metabolic diseases in a male that result in insufficient sperm production and the inability of a female's ovaries to produce or release ova. In addition, pituitary disorders may cause infertility in both sexes because the gonads are responsive to regulation by pituitary hormones such as follicle-stimulating hormone and luteinizing hormone. However, clinical conditions exist in which an infertile female is still capable of ovulating. Therefore, the ovary may respond to additional signals that are not yet identified.

Zhang et al. (1994, *Nature* 372:425–432) describe the cloning and sequencing of the mouse ob gene and its human homolog. In an effort to understand the physiologic function of the ob gene, several independent research groups produced recombinant ob gene product in bacteria for in vivo testing (Pelleymounter et al., 1995, *Science* 269:540–543; Halaas et al., 1995, *Science* 269:543–546; Campfield et al., 1995, *Science* 269:546–549). When the Ob protein (also known as leptin) was injected into grossly obese mice, which possessed two mutant copies of the ob gene, the mice exhibited a reduced appetite and began to lose weight. Similarly, when normal mice received leptin, they also ate less than the untreated controls. Interestingly, when leptin was administered to ob/ob female mice which were always infertile, fertility was restored in these animals (Chehab et al., 1996, *Nature Genetics* 12:318–320).

Recently, a leptin fusion protein was generated and used to screen for the leptin receptor (also known as OB-R) in a cDNA expression library prepared from mouse choroid plexus, a tissue that lines brain cavities termed ventricles (Tartaglia, 1995, *Cell* 83:1263–1271). This approach led to the cloning of one form of the OB-R coding sequence, which reveals a single membrane-spanning receptor, sharing structural similarities with several Class I cytokine receptors, such as the gpl130 signal-transducing component of the interleukin-6 receptor (Taga et al., 1989, *Cell* 58:573–581), the granulocyte-colony stimulating factor receptor (Fukunaga et al., 1990, *Cell* 61:341–350), and the leukemia inhibitory factor receptor (Gearing et al., 1991, *EMBO J.* 10:2839–2848). Northern blot analysis and reverse transcription-polymerase chain reaction (RT-PCR) demonstrate that OB-R mRNA is expressed in several tissues, including lung, kidney, total brain, choroid plexus and hypothalamus.

The reported mouse OB-R protein contains a relatively short intracellular cytoplasmic domain as compared with other Class I cytokine receptors. Subsequently, when cDNA encoding its human homolog was isolated from a human infant brain library, the predicted human protein sequence contains a much longer intracellular domain. In view of this finding, it was speculated that different forms of the receptor might exist (Barinaga, 1996, *Science* 271:29). However, prior to the resent invention, there was no report on how variant forms of the OB-R in humans would relate to infertility.

SUMMARY OF THE INVENTION

The present invention relates to variant forms of the human OB-R. In particular, it relates to the detection of these receptor variants in reproductive organs such as the ovary and the prostate gland for diagnosis of the cause of infertility, and methods for treating infertility by targeting these variant receptors.

The invention is based, in part, upon the Applicants' discovery of human cDNA clones encoding three variant forms of the OB-R. These receptors differ structurally from a reported OB-R with only three amino acid substitutions in the extracellular domain, but extensive diversity is observed in their intracellular cytoplasmic domains at the 3' end. The cytoplasmic domains of the variants of the invention are both shorter and distinct in nucleotide sequence from the corresponding domain of the published form of OB-R (Tartaglia et al., 1995 *Cell* 83:1263). In addition, the cytoplasmic domain of one such variant is highly homologous to a human retrotransposon sequence. The OB-R variants described herein represent incomplete receptors which may be incompetent or partially competent in transducing signals upon ligand binding. Expression of the different forms of the receptor have been detected in prostate and ovary. Furthermore, leptin activity has been shown to be naturally present in ovarian follicular fluids. Therefore, a wide variety of uses are encompassed by the present invention, including but not limited to, the detection of the receptor variants in reproductive organs for the diagnosis of infertility, methods to inhibit and/or down-regulate the expression of these receptor variants, gene therapy to replace the receptor variants in homozygous individuals, and direct activation of downstream signal transduction pathways in cells expressing the defective receptor variants for improving fertility.

BRIEF DESCRIPTION OF THE DRAWINGS

FIGS. 1A–1E. Nucleotide sequence and deduced amino acid sequence of Form 1 the human OB-R variant (SEQ ID NO:1).

The amino acid sequence (SEQ ID NOS:2,3&4) diverges from the human OB-R reported by Tartaglia et al. (1995, *Cell* 83:1263–1271) at nucleotide residue #349, #422, #764 and from residue #2770 and beyond.

FIG. 2. Nucleotide sequence comparison between human OB-R variant Form 1 (SEQ. ID NO:5), Form 2 (SEQ ID NO:6) and Form 3 (SEQ ID NO: 7), at the 3'end.

FIGS. 3A–3D. Amino acid sequence comparison between OB-R variant Forms 1 (HuB1.219–1) (SEQ. ID NO: 8), 2 (HuB1.219–2), (SEQ ID NO: 9) 3 (HuB1.219–3) (SEQ ID NO: 10), human OB-R (HuOBR) (SEQ ID NO:11) published by Tartaglia et al., 1995, Cell 83:1263; and murine OB-R (MuOBR) (SEQ ID NO:12).

Figure 4:
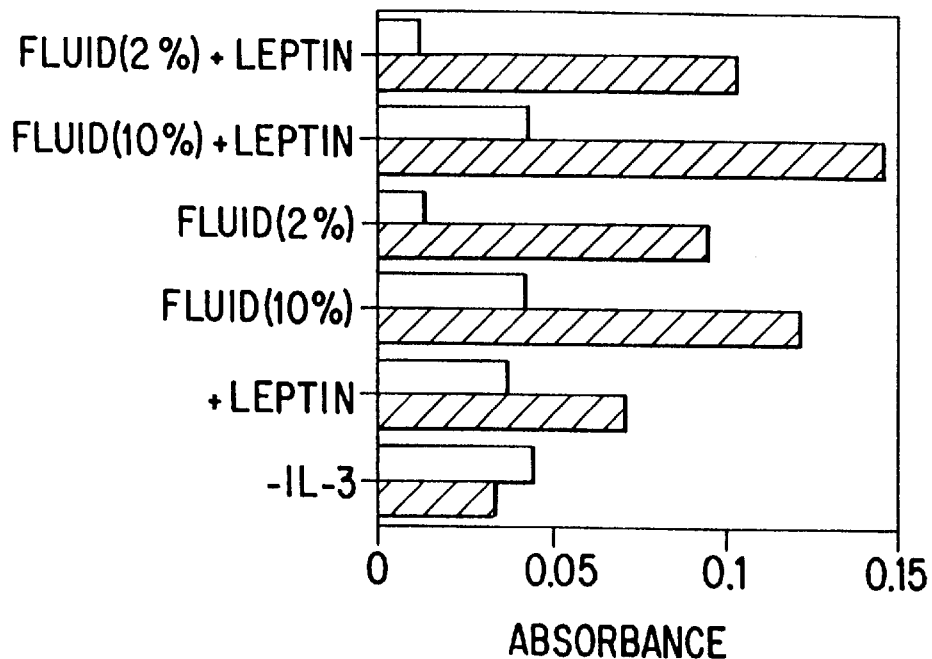

FIG. 4. Proliferation of BaF3 cells and cells transfected with chimeric OB-R in the presence of follicular fluids. ■=transfected cell line; ▫=BaF3 parent cell line.

Figure 5:
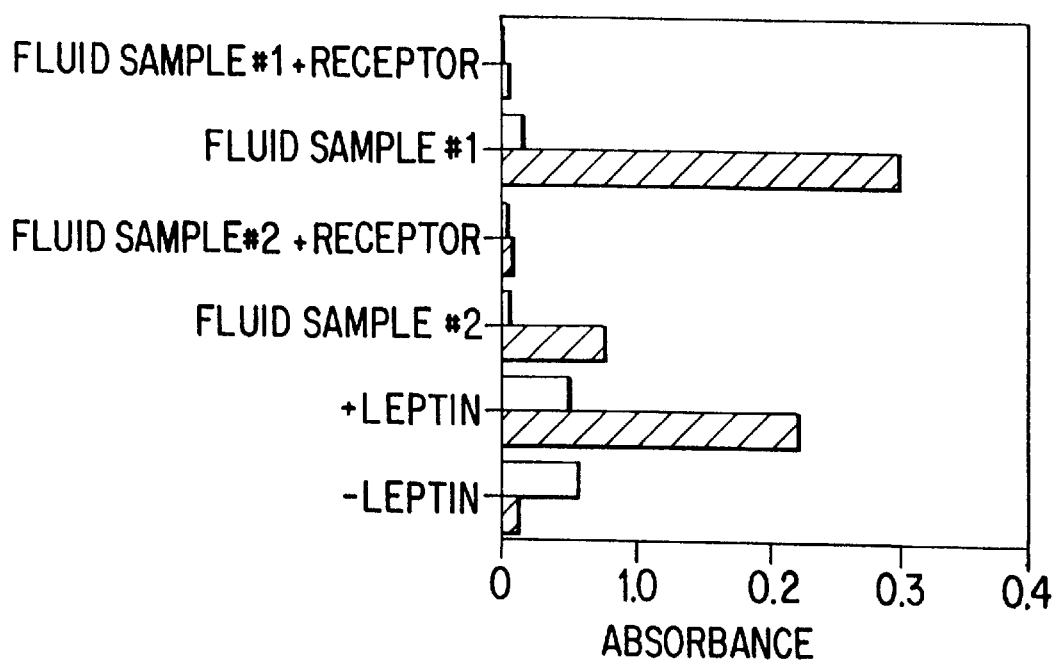

FIG. 5. Proliferation of transfected BaF3 cell line in the presence of follicular fluids is inhibited by soluble OB-R, indicating that leptin is the active growth-inducing substance in the fluids. ■=transfected cell line; ▫=BaF3 parent cell line.

DETAILED DESCRIPTION OF THE INVENTION

THE OB-R VARIANTS

The present invention relates to nucleic acid and amino acid sequences of OB-R variants. In a specific embodiment by way of example in Section 6, infra, three variants were cloned and characterized. Amino acid sequence comparison of these OB-R variants with a published human OB-R sequence (Tartaglia et al., 1995, Cell 83:1263–1271) reveals three amino acid differences in their extracellular domains and extensive diversity in their intracellular cytoplasmic domains. More specifically, FIGS. 1A–1E shows that in the variants, nucleotide residues #349–351 encode alanine, nucleotide residues #421–423 encode arginine and nucleotide residues #763–765 encode arginine. Additionally, the variants diverge both in length and sequence composition from the human OB-R sequence published by Tartaglia et al. from nucleotide residue #2770 and beyond (FIG. 2). In this regard, the intracellular domain of Form 1 (FIGS. 1A–1E) of the variants is highly homologous to a retrotransposon sequence (Ono et al., 1987, Nucl. Acid. Res. 15:8725–8737). Such variants represent functionally defective forms of human OB-R in signal transduction upon leptin binding.

In order to clone additional variant forms of the molecule, labeled DNA probes made from nucleic acid fragments corresponding to any portion of the cDNA disclosed herein may be used to screen a cDNA library prepared from human ovary, human prostate, human fetal liver, human lung, human kidney, human choroid plexus and human hypothalamus. More specifically, oligonucleotides corresponding to either the 5' or 3' terminus of the cDNA sequence may be used to obtain longer nucleotide sequences. Briefly, the library may be plated out to yield a maximum of 30,000 pfu for each 150 mm plate. Approximately 40 plates may be screened. The plates are incubated at 37° C. until the plaques reach a diameter of 0.25 mm or are just beginning to make contact with one another (3–8 hours). Nylon filters are placed onto the soft top agarose and after 60 seconds, the filters are peeled off and floated on a DNA denaturing solution consisting of 0.4 N sodium hydroxide. The filters are then immersed in neutralizing solution consisting of 1 M Tris HCL, pH 7.5, before being allowed to air dry. The filters are prehybridized in casein hybridization buffer containing 10% dextran sulfate, 0.5 M NaCl, 50 mM Tris HCL, pH 7.5, 0.1% sodium pyrophosphate, 1% casein, 1% SDS, and denatured salmon sperm DNA at 0.5 mg/ml for 6 hours at 60° C. The radiolabelled probe is then denatured by heating to 95° C. for 2 minutes and then added to the prehybridization solution containing the filters. The filters are hybridized at 60° C. for 16 hours. The filters are then washed in 1X wash mix (10X wash mix contains 3 M NaCl, 0.6 M Tris base, and 0.02 M EDTA) twice for 5 minutes each at room temperature, then in 1X wash mix containing 1% SDS at 60° C. for 30 minutes, and finally in 0.3X wash mix containing 0.1% SDS at 60° C. for 30 minutes. The filters are then air dried and exposed to x-ray film for autoradiography. After developing, the film is aligned with the filters to select a positive plaque. If a single, isolated positive plaque cannot be obtained, the agar plug containing the plaques will be removed and placed in lambda dilution buffer containing 0.1 M NaCl, 0.01 M magnesium sulfate, 0.035 M Tris Hcl, pH 7.5, 0.01% gelatin. The phage may then be replated and rescreened to obtain single, well isolated positive plaques. Positive plaques may be isolated and the cDNA clones sequenced using primers based on the known cDNA sequence. This step may be repeated until a full length cDNA is obtained.

One method for identifying all 3' isoforms is to PCR amplify the 3' ends of the variant cDNA from a variety of tissues including but not limiting to, choroid plexus, hypothalamus, fetal liver, bone marrow, ovary, or prostate. To obtain the 3' end of the cDNA, an oligo-dT primer is used to synthesize the cDNA first strand. OB-R specific primers from the conserved region of the gene (e.g. up stream of nucleotide 2770) and oligo-dT are then used to amplify the 3' end. The PCR fragments are cloned and sequenced by standard techniques. Once obtained, these sequences may be translated into amino acid sequence and examined for certain landmarks such as continuous open reading frame, regulatory regions that associate with tyrosine kinase activation, and finally overall structural similarity to known OB-R variants. These 3' variants may represent additional signal transduction defective forms of OB-R.

EXPRESSION OF THE OB-R VARIANTS

In accordance with the invention, the OB-R variant polynucleotide sequence which encodes a protein, peptide fragments, fusion proteins or functional equivalents thereof, may be used to generate recombinant DNA molecules that direct the expression of the protein, peptide fragments, fusion proteins or a functional equivalent thereof, in appropriate host cells. Such polynucleotide sequences, as well as other polynucleotides which selectively hybridize to at least a part of such polynucleotides or their complements, may also be used in nucleic acid hybridization assays, Southern and Northern blot analyses, etc.

Due to the inherent degeneracy of the genetic code, other DNA sequences which encode substantially the same or a functionally equivalent amino acid sequence, may be used in the practice of the invention for the expression of the OB-R variant. Such DNA sequences include those which are capable of hybridizing to the OB-R variant sequence under stringent conditions, particularly at its 3' end. The phrase "stringent conditions" as used herein refers to those hybridizing conditions that (1) employ low ionic strength and high temperature for washing, for example, 0.015 M NaCl/0.0015 M sodium citrate/0.1% SDS at 50° C.; (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at PH 6.5 with 750 mM NaCl, 75 mM sodium citrate at 42° C.; or (3) employ 50% formamide, 5×SSC (0.75 M NaCl, 0.075 M Sodium pyrophosphate, 5×Denhardt's solution, sonicated salmon sperm DNA (50 μg/ml), 0.1% SDS, and 10% dextran sulfate at 42° C., with washes at 42° C. in 0.2×SSC and 0.1% SDS.

Altered DNA sequences which may be used in accordance with the invention include deletions, additions or substitutions of different nucleotide residues resulting in a sequence that encodes the same or a functionally equivalent gene product. The gene product itself may contain deletions, additions or substitutions of amino acid residues within the OB-R variant sequence, which result in a silent change thus producing a functionally equivalent protein. Such amino acid substitutions may be made on the basis of similarity in polarity, charge, solubility, hydrophobicity, hydrophilicity, and/or the amphipathic nature of the residues involved. For example, negatively charged amino acids include aspartic acid and glutamic acid; positively charged amino acids include lysine, histidine and arginine; amino acids with uncharged polar head groups having similar hydrophilicity values include the following: glycine, asparagine, glutamine, serine, threonine, tyrosine; and amino acids with nonpolar head groups include alanine, valine, isoleucine, leucine, phenylalanine, proline, methionine, tryptophan.

The DNA sequence of the invention may be engineered in order to alter the OB-R variant coding sequence for a variety of ends, including but not limited to, alterations which modify processing and expression of the gene product. For example, mutations may be introduced using techniques which are well known in the art, e.g., site-directed mutagenesis, to insert new restriction sites, to alter glycosylation patterns, phosphorylation, etc. In addition, the intracellular domain may also be altered and replaced by a different domain, such as the OB-R intracellular domain by Tartaglia et al.

In another embodiment of the invention, the OB-R variant sequence may be ligated to a heterologous sequence to encode a fusion protein. For example, for screening of peptide libraries for inhibitors or stimulators of receptor activity, it may be useful to encode a chimeric protein expressing a heterologous epitope that is recognized by a commercially available antibody. A fusion protein may also be engineered to contain a cleavage site located between the OB-R variant sequence and the heterologous protein sequence, so that the variant may be cleaved away from the heterologous moiety.

In an alternate embodiment of the invention, the coding sequence of the OB-R variant could be synthesized in whole or in part, using chemical methods well known in the art. (See, for example, Caruthers et al., 1980, *Nuc. Acids Res. Symp. Ser.* 7:215–233; Crea and Horn, 180, *Nuc. Acids Res.* 9(10):2331; Matteucci and Caruthers, 1980, *Tetrahedron Letters* 21:719; and Chow and Kempe, 1981, *Nuc. Acids Res.* 9(12):2807–2817). Alternatively, the protein itself could be produced using chemical methods to synthesize OB-R variant amino acid sequence in whole or in part. For example, peptides can be synthesized by solid phase techniques, cleaved from the resin, and purified by preparative high performance liquid chromatography. (e.g., see Creighton, 1983, *Proteins Structures And Molecular Principles,* W. H. Freeman and Co., N.Y. pp. 50–60). The composition of the synthetic peptides may be confirmed by amino acid analysis or sequencing (e.g., the Edman degradation procedure; see Creighton, 1983, *Proteins, Structures and Molecular Principles,* W. H. Freeman and Co., N.Y., pp. 34–49).

In order to express the OB-R variant in host cells, the nucleotide sequence coding for the variant, or a functional equivalent, is inserted into an appropriate expression vector, i.e., a vector which contains the necessary elements for the transcription and translation of the inserted coding sequence. The expressed gene products as well as host cells or cell lines transfected or transformed with recombinant OB-R variant expression vectors can be used for a variety of purposes. For example, host cells expressing the OB-R variant may be used to verify the ability of this molecule to bind leptin in a binding assay with radiolabeled, enzyme-conjugated or fluorescent dye-conjugated leptin. At the same time, the ability of the molecule to transduce an activation signal in host cells upon binding to leptin may be tested by assaying proliferation or phosphorylation pattern of kinases in the cells. In addition, genetically-engineered host cells can be used to screen for and select agonist and antagonist compounds, including any inhibitors that would interfere with binding of leptin to the extracellular or intracellular domain of the OB-R variant. In that connection, such host cells may be used to screen for and select small molecules i.e., peptides, nucleic acids and synthetic compounds that can supplement the incomplete signal transduced by the OB-R variant following leptin binding. Such small molecules may also affect receptor isoform pairing, thereby modifying the ability of OB-R to respond to leptin. Other uses, include, but are not limited to generating antibodies (i.e., monoclonal or polyclonal) that competitively inhibit activity of an OB-R variant, neutralize its activity, or even enhances it activity. Antibodies may be used in detecting and quantifying expression of OB-R levels in cells and tissues.

USES OF OB-R VARIANT POLYNUCLEOTIDES

An OB-R variant polynucleotide may be used for diagnostic and/or therapeutic purposes. For diagnostic purposes, an OB-R variant polynucleotide may be used to detect gene expression or aberrant gene expression in infertile individuals as well as in normal individuals to identify predisposition for infertility. Included in the scope of the invention are oligonucleotide sequences, that include antisense RNA and DNA molecules, ribozymes and triplex DNA, that function to inhibit translation of OB-R variant.

DIAGNOSTIC USES OF OB-R VARIANT POLYNUCLEOTIDES

An OB-R variant polynucleotide may have a number of uses for the diagnosis of the possible causes underlying infertility, resulting from expression of a defective receptor variant. For example, the OB-R variant cytoplasmic domain DNA sequence may be used in hybridization assays of biopsy or autopsy materials obtained from ovary or prostate to diagnose OB-R variant expression; e.g., Southern or Northern analysis, including in situ hybridization assays as well as PCR. Such techniques are well known in the art, and are in fact the basis of many commercially available diagnostic kits. For PCR detection, primers may be designed from a conserved region of the coding sequence and within the 3' region of OB-R variant. The tissues suitable for such analysis include but are not limited to, prostate, ovary, and testes, ova, sperm (semen), and cells in the ovarian follicular fluids.

THERAPEUTIC USES OF OB-R VARIANT POLYNUCLEOTIDES

An OB-R variant polynucleotide may be useful in the treatment of infertile conditions. By introducing gene sequences into cells, gene therapy can be used to treat conditions in which the cells do not respond to leptin normally due to expression of a defective OB-R variant. In some instances, the polynucleotide encoding a functional OB-R is intended to replace or act in the place of the functionally defective OB-R variant gene. Alternatively, abnormal conditions characterized by expression of two copies of the OB-R variant can be treated using the gene therapy techniques described below.

Non-responsiveness to normal levels of leptin may contribute to infertility. This may result from a functionally defective receptor that does not transduce competent signals upon ligand binding. Recombinant gene therapy vectors, such as viral vectors, may be engineered to express signalling competent forms of OB-R which may be used to augment the non-responsiveness of the naturally occurring OB-R variant. A signalling competent form may be, for example, a protein with the same extracellular domain and transmembrane region, but containing all or part of its normal signal transduction domain, such as that described by Tartaglia et al. (1995, *Cell* 83:1263–1271). Thus, recombinant gene therapy vectors may be used therapeutically for treatment of infertility resulting from expression or activity of the OB-R variant. Accordingly, the invention provides a method of augmenting signal transduction by an endogenous OB-R variant in a cell comprising delivering a DNA molecule encoding a signalling competent form of the OB-R to the cell so that the signalling competent protein is produced in the cell and competes with the endogenous defective OB-R variant for access to molecules in the signalling pathway which does not activate or are not activated by the endogenous natural defective receptor. Additionally, since dimerization of a functional receptor with a defective variant may occur in cells of heterozygous individuals, small molecules may be used to inhibit such pairing, thereby increasing the number of functional dimeric receptors for proper signalling in response to leptin.

Expression vectors derived from viruses such as retroviruses, vaccinia virus, adeno-associated virus, herpes viruses, or bovine papilloma virus, may be used for delivery of recombinant functional OB-R into the targeted cell population. Methods which are well known to those skilled in the art can be used to construct recombinant viral vectors containing an OB-R polynucleotide sequence. See, for example, the techniques described in Sambrook et al., 1989, *Molecular Cloning A Laboratory Manual,* Cold Spring Harbor Laboratory, N.Y. and Ausubel et al., 1989, *Current Protocols in Molecular Biology,* Greene Publishing Associates and Wiley Interscience, N.Y. Alternatively, recombinant OB-R molecules can be reconstituted into liposomes for delivery to target cells.

Oligonucleotide sequences including anti-sense RNA and DNA molecules and ribozymes that function to inhibit the translation of the OB-R variant mRNA are within the scope of the invention. Anti-sense RNA and DNA molecules act to directly block the translation of mRNA by binding to targeted mRNA and preventing protein translation. In regard to antisense DNA, oligodeoxyribonucleotides derived from the OB-R variant nucleotide sequence at nucleotide #2771 and beyond, are preferred.

Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Within the scope of the invention are engineered hammerhead motif ribozyme molecules that specifically and efficiently catalyze endonucleolytic cleavage of OB-R variant RNA sequences.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features such as secondary structure that may render the oligonucleotide sequence unsuitable. The suitability of candidate targets may also be evaluated by testing their accessibility to hybridization with complementary oligonucleotides, using ribonuclease protection assays.

Oligodeoxyribonucleotides can form sequence-specific triple helices by hydrogen bonding to specific complementary sequences in duplexed DNA. Interest in triple helices has focused on the potential biological and therapeutic applications of these structures. Formation of specific triple helices may selectively inhibit the replication and/or gene expression of targeted genes by prohibiting the specific binding of functional trans-acting factors.

Oligonucleotides to be used in triplex helix formation should be single stranded and composed of deoxynucleotides. The base composition of these oligonucleotides must be designed to promote triple helix formation via Hoogsteen base pairing rules, which generally require sizeable stretches of either purines or pyrimidines to be present on one strand of a duplex. Oligonucleotide sequences may be pyrimidine-based, which will result in TAT and CGC triplets across the three associated strands of the resulting triple helix. The pyrimidine-rich oligonucleotides provide base complementarily to a purine-rich region of a single strand of the duplex in a parallel orientation to that strand. In addition, oligonucleotides may be chosen that are purine-rich, for example, containing a stretch of G residues. These oligonucleotides will form a triple helix with a DNA duplex that is rich in GC pairs, in which the majority of the purine residues are located on a single strand of the targeted duplex, resulting in GGC triplets across the three strands in the triplex. Alternatively, the potential sequences that can be targeted for triple helix formation may be increased by creating a so called "switchback" oligonucleotide. Switchback oligonucleotides are synthesized in an alternating 5'-3', 3'-5' manner, such that they base pair with first one strand of a duplex and then the other, eliminating the necessity for a sizeable stretch of either purines or pyrimidines to be present on one strand of a duplex.

Both anti-sense RNA and DNA molecules and ribozymes of the invention may be prepared by any method known in the art for the synthesis of RNA molecules. These include techniques for chemically synthesizing oligodeoxyribonucleotides well known in the art such as solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various modifications to the DNA molecules may be introduced as a means of increasing intracellular stability and half-life. Possible modifications include but are not limited to the addition of flanking sequences of ribo- or deoxy- nucleotides to the 5' and/or 3' ends of the molecule or the use of phosphorothioate or 2' O-methyl rather than phosphodiesterase linkages within the oligodeoxyribonucleotide backbone.

ACTIVATION OF TYROSINE KINASE PATHWAYS IN INFERTILITY

Many known class I cytokine receptors initiate cell signaling via Janus kinases (JAKs) (Ihle, 1995, *Nature* 5

377:591–594; Heldin, 1995, *Cell* 80:213–223; Kishimoto et al, 1994, *Cell* 76:253–62; Ziemiecki et al, 1994, *Trends Cell. Biol.* 4:207–212). JAK1–3 have been shown to bind to conserved sequences termed box1 and box2 (Fukunaga et al., 1991, *EMBO J.* 10:2855–65; Murakami, 1991, *Proc. Natl. Acad. Sci. USA* 88:11349–53). Ligand binding induces a homo- or hetero-dimerization of receptor chains which activates, by phosphorylation, the JAKs. The activated JAKs, in turn, phosphorylate members of the STAT family (Heldin, 1995, *Cell* 80:213–223; Kishimoto et al., *Blood* 86:1243–54; Darnell et al., 1994, *Science* 264:1415–21; Zhong et al, 1994, *Proc. Natl. Acad. Sci. USA* 91:4806–10; Hou et al., 1994, *Science* 265:1701–6). These phosphorylated STATs ultimately translocate to the nucleus, form transcription complexes, and regulate gene expression. Both box1 and box2 are required for complete signaling in certain systems. (Fukunaga et al., 1991, *EMBO J.* 10:2855–65; Murakami, 1991, *Proc. Natl. Acad. Sci. USA* 88:11349–53).

The OB-R variants disclosed herein have a typical box1 (from nucleotide #2707–2730) that contains the critical xWxxxPxP amino acid sequence, but they do not contain an obvious box2 nor further downstream sequences that are important for normal receptor activation. Therefore, it is possible to use compounds that activate JAKs to directly activate these pathways for improving fertility without triggering the OB-R.

EXAMPLE: MOLECULAR CLONING OF OB-R VARIANTS

A number of cDNA clones were isolated from a human fetal liver cDNA library (Clontech, Palo Alto, Calif.), and the DNA sequences of several of these clones were determined. These clones (designated as Hu-B1.219 #4, #33, #34, #1, #3, #8, #36, #55, #57, #60 and #62) contained overlapping sequences, which were then compiled into a contiguous nucleotide sequence referred to as Hu-B1.219. When the deduced amino acid sequence of one such sequence (FIGS. 1A–1E) was compared with the sequence of a recently published human OB-R (Tartaglia et al., 1995, *Cell* 83:1263), they were shown to be nearly identical in the extracellular domains with the exception of three amino acids, whereas there existed extensive diversity in their intracellular cytoplasmic domains at the 3' end. This sequence encodes an OB-R variant herein referred to as Form 1. In addition, two other variants were identified, and they both differ from the human OB-R published by Tartaglia et al (1995, *Cell* 83:1263) in their 3' ends (FIG. 2). These two additional variants are referred to as Forms 2 and 3 of OB-R. The predicted protein sequences of the variants (FIGS. 3A–3D) contain two FN III domains, each containing a "WS box", which are characteristic of genes of the Class I cytokine receptor family.

When various human tissue RNA were probed with a fragment containing a sequence commonly shared by the OB-R variants by Northern blot analysis, expression was detected in heart, placenta, lung, liver, muscle, pancreas, prostate, ovary, small intestine and brain (Table I).

Based on the sequence presented in FIGS. 1A–1E, the translation initiation site appears at position #97. The sequences of Forms 1, 2 and 3 encode an open reading frame up to and including nucleotide #2970, #2814 and #2784 (FIG. 2), respectively. It is believed that the sequence between nucleotides #2629 and #2682 (FIGS. 1A–1E) encodes a transmembrane domain. The complete sequences of Forms 1, 2 and 3 encode proteins of 958, 906 and 896 amino acids, respectively.

TABLE I

SUMMARY OF NORTHERN BLOT ANALYSIS OF OB-R EXPRESSION IN HUMAN TISSUES AND CELL LINES

| Developmental Stage | Tissue Type | Expression |
|---|---|---|
| fetal | brain | – |
|  | lung | +++ |
|  | liver | +++++ |
|  | kidney | + |
| adult | heart | ++ |
|  | brain | +/– |
|  | placenta | + |
|  | lung | + |
|  | liver | +++ |
|  | skeletal muscle | + |
|  | kidney | +/– |
|  | pancreas | + |
|  | spleen | +/– |
|  | thymus | +/– |
|  | prostate | ++ |
|  | testis | +/– |
|  | ovary | +++ |
|  | small intestine | ++ |
|  | colon | – |
|  | peripheral blood leukocytes | – |
| cancer | HL-60 | – |
|  | HeLa | – |
|  | K-562 | +++ |
|  | MOLT-4 | – |
|  | Raji | – |
|  | SW480 | – |
|  | A549 | + |
|  | G361 | – |

The sequences of the three OB-R variants are identical to the sequence of human OB-R reported by Tartaglia (1995, *Cell* 83:1263–1271) in the transmembrane region and a portion of the intracellular domain up to and including nucleotide #2769 (FIG. 2), then they diverge at nucleotide #2770 and beyond. In addition, the products of these cDNA are substantially shorter in their intracellular domain than the human OB-R published by Tartaglia et al. These isoforms of OB-R may derive from a common precursor mRNA by an alternative splicing mechanism. The sequence in this region is consistent with well known splice junctions. It is noteworthy that the DNA sequence of Form 1 (FIGS. 1A–1E) of the OB-R variant from nucleotide #2768 to the end is 98% identical to a human retrotransposon sequence that is thought to be derived from a human endogenous retroviral DNA sequence (Singer, 1982, *Cell* 28:433; Weiner et al., 1986, *Ann. Rev. Biochem.* 55:631; Lower et al., 1993, *Proc. Natl. Acad. Sci. USA* 90:4480; Ono et al., 1987, *Nucl. Acid. Res.* 15:8725–8735).

EXAMPLE: EXPRESSION OF OB-R IN SEX HORMONE PRODUCING CELLS IN TEE OVARY AND DETECTION OF LEPTIN IN OVARIAN FOLLICULAR FLUIDS

MATERIALS AND METHODS

REVERSE TRANSCRIPTION/POLYMERASE CHAIN REACTION (RT/PCR)

Total RNA was isolated using standard laboratory procedures (Sambrook et al., 1989, *Molecular Cloning, A Laboratory Manual*, Cold Spring Harbor Laboratory, N.Y.). Approximately 1 μg of total RNA was reverse transcribed and the cDNA was amplified by PCR (Perkin Elmer, Norwalk, Conn.). The PCR amplification conditions were:

94° C. for 30 sec, 60° C. for 30 sec, 72° C. for 30 sec for a total of 40 cycles. The amplified products were resolved by agarose gel electrophoresis and visualized by ethidium bromide staining. The OB-R amplimers were GGTTTG-CATATGGAAGTC (upper) (SEQ ID NO:13) and CCT-GAACCATCCAGTCTCT (lower) (SEQ ID NO:14). The Form 1 specific amplimers were GACTCATTGTGCAGT-GTTCAG (upper) (SEQ ID NO:15) and TAGTGGAGG-GAGGGTCAGCAG (lower) (SEQ ID NO:16).

RESULTS

Table I in Section 6, supra, shows that the OB-R is expressed in reproductive organs such as ovary and prostate gland. In order to determine the specific cell types in the ovary that expressed the receptor, primary granulosa and cumulus cell cultures were established from the ovaries and assayed for OB-R expression by RT/PCR. In Table II, the cells that produced sex hormones in the ovary, i.e. granulosa and cumulus cells, expressed the different forms of OB-R.

TABLE II

OB-R EXPRESSION IN GRANULOSA AND CUMULUS CELLS BY RT/PCR

| Cell Types | Form 1 | Form 3 | OB-R* |
|---|---|---|---|
| Granulosa cells derived from ovarian follicles | + | + | +/− |
| Granulosa cells derived from ovarian follicles | − | + | + |
| Cumulus cells derived from oocytes | + | + | + |

*OB-R refers to the published sequence by Tartaglia (1995, Cell 83:1263–1271).

Additionally, ovarian follicular fluids were obtained from several patients and assayed for the presence of leptin. The detection assay utilized an interleukin-3-dependent cell line, BaF3, that had been transfected with a chimeric receptor construct containing the extracellular domain of murine OB-R ligated to the transmembrane and cytoplasmic domains of the thrombopoietin receptor. Both the BaF3 parental cell line and the transfected cell line responded to IL-3, whereas only the transfected cells responded to leptin (FIG. 4).

When the cells were incubated with follicular fluids, the transfected cell line was induced to proliferate as compared with the parental cell line as a control (FIG. 4). The cell growth-stimulating activity in the fluids was shown to be leptin since the activity was specifically inhibited by the addition of soluble murine OB-R (FIG. 5). Therefore, leptin is present in the follicular fluids, and it stimulates OB-R-expressing cells in the ovary to proliferate.

DEPOSIT OF MICROORGANISMS

The following organisms were deposited with the American Type Culture Collection (ATCC), 12301 Parklawn Drive, Rockville, Md. 20852.

| Strain Designation | Accession No. |
|---|---|
| HuB1.219, #1 | 75885 |
| HuB1.219, #4 | 75886 |
| HuB1.219, #8 | 75887 |
| HuB1.219, #33 | 75888 |
| HuB1.219, #34 | 75889 |
| HuB1.219, #36 | 75890 |
| HuB1.219, #55 | 75971 |
| HuB1.219, #60 | 75973 |
| HuB.1.219, #3 | 75970 |
| HuB1.219, #57 | 75972 |
| HuB1.219, #62 | 75974 |

The present invention is not to be limited in scope by the exemplified embodiments, which are intended as illustrations of individual aspects of the invention. Indeed, various modifications for the invention in addition to those shown and described herein will become apparent to those skilled in the art from the foregoing description and accompanying drawings. Such modifications are intended to fall within the scope of the appended claims.

All publications cited herein are incorporated by reference in their entirety.

What is claimed is:

1. A method for detecting a nucleic acid molecule encoding a leptin receptor variant in a cell of a reproductive organ, comprising:
   (a) contacting a nucleic acid molecule from the cell with a polynucleotide selected from the group consisting of
      (i) nucleotides #20 through #241 of SEQ ID NO:5;
      (ii) the complement of the polynucleotide of (i);
      (iii) a portion of the polynucleotide of (i) that specifically hybridizes to a nucleic acid comprising the polynucleotide of (ii); and
      (iv) a portion of the polynucleotide of (ii) that specifically hybridizes to a nucleic acid comprising the polynucleotide of (i); and
   (b) detecting specific hybridization of the polynucleotide with the nucleic acid molecule.

2. The method of claim 1 in which the polynucleotide of step (a) is selected from the group consisting of
   (i) nucleotides #20 through #220 of SEQ ID NO: 5;
   (ii) the complement of the polynucleotide of (i);
   (iii) a portion of the polynucleotide of (i) that specifically hybridizes to a nucleic acid comprising the polynucleotide of (ii); and
   (iv) a portion of the polynucleotide of (ii) that specifically hybridizes to a nucleic acid comprising the polynucleotide of (i).

3. The method of claim 1 in which the nucleic acid molecule is ribonucleic acid.

4. The method of claim 3 in which the ribonucleic acid is first extracted from the cell.

5. The method of claim 1 in which the nucleic acid molecule is deoxyribonucleic acid.

6. The method of claim 5 in which the deoxyribonucleic acid is first extracted from the cell.

7. The method of claim 1 in which the hybridization is detected by an in situ hybridization method.

8. The method of claim 1 in which the hybridization is detected by a Northern blot method.

9. The method of claim 1 in which the polynucleotide of step (a) is used as a primer in an amplification method.

10. The method of claim 9 in which the method is polymerase chain reaction.

11. The method of claim 1 in which the cell is obtained from ovary.

12. The method of claim 1 in which the cell is obtained from prostate.

13. The method of claim 1 in which the cell is obtained from testis.

14. The method of claim 1 in which the cell is a sperm.

15. The method of claim 1 in which the cell is an ovum.

16. The method of claim 1 in which the cell is obtained from ovarian follicular fluids.

17. A method for detecting a nucleic acid molecule encoding a leptin receptor variant in a cell of a reproductive organ, comprising:
(a) contacting a nucleic acid molecule from the cell with a polynucleotide selected from the group consisting of
(i) nucleotides #20 through #130 of SEQ ID NO:6;
(ii) the complement of the polynucleotide of (i);
(iii) a portion of the polynucleotide of (i) that specifically hybridizes to a nucleic acid comprising the polynucleotide of (ii); and
(iv) a portion of the polynucleotide of (ii) that specifically hybridizes to a nucleic acid comprising the polynucleotide of (i); and
(b) detecting specific hybridization of the polynucleotide with the nucleic acid molecule.

18. The method of claim 17 in which the polynucleotide of step (a) is selected from the group consisting of
(i) nucleotides #20 through #64 of SEQ ID NO:6;
(ii) the complement of the polynucleotide of (i):
(iii) a portion of the polynucleotide of (i) that specifically hybridizes to a nucleic acid comprising the polynucleotide of (ii); and
(iv) a portion of the polynucleotide of (ii) that specifically hybridizes to a nucleic acid comprising the polynucleotide of (i).

19. The method of claim 17 in which the nucleic acid molecule is ribonucleic acid.

20. The method of claim 19 in which the ribonucleic acid is first extracted from the cell.

21. The method of claim 17 in which the nucleic acid molecule is deoxyribonucleic acid.

22. The method of claim 21 in which the deoxyribonucleic acid is first extracted from the cell.

23. The method of claim 17 in which the hybridization is detected by an in situ hybridization method.

24. The method of claim 17 in which the hybridization is detected by a Northern blot method.

25. The method of claim 17 in which the polynucleotide of step (a) is used as a primer in an amplification method.

26. The method of claim 25 in which the method is polymerase chain reaction.

27. The method of claim 17 in which the cell is obtained from ovary.

28. The method of claim 17 in which the cell is obtained from prostate.

29. The method of claim 17 in which the cell is obtained from testis.

30. The method of claim 17 in which the cell is a sperm.

31. The method of claim 17 in which the cell is an ovum.

32. The method of claim 17 in which the cell is obtained from ovarian follicular fluids.

33. A method for detecting a nucleic acid molecule encoding a leptin receptor variant in a cell of a reproductive organ, comprising:
(a) contacting a nucleic acid molecule from the cell with a polynucleotide selected from the group consisting of
(i) nucleotides #20 through #127 of SEQ ID NO:7;
(ii) the complement of the polynucleotide of (i);
(iii) a portion of the polynucleotide of (i) that specifically hybridizes to a nucleic acid comprising the polynucleotide of (ii); and
(iv) a portion of the polynucleotide of (ii) that specifically hybridizes to a nucleic acid comprising the polynucleotide of (i); and
(b) detecting specific hybridization of the polynucleotide with the nucleic acid molecule.

34. The method of claim 33 in which the polynucleotide of step (a) is selected from the group consisting of
(i) nucleotides #20 through #34 of SEQ ID NO:7;
(ii) the complement of the polynucleotide of (i);
(iii) a portion of the polynucleotide of (i) that specifically hybridizes to a nucleic acid comprising the polynucleotide of (ii); and
(iv) a portion of the polynucleotide of (ii) that specifically hybridizes to a nucleic acid comprising the polynucleotide of (i).

35. The method of claim 33 in which the nucleic acid molecule is ribonucleic acid.

36. The method of claim 35 in which the ribonucleic acid is first extracted from the cell.

37. The method of claim 33 in which the nucleic acid molecule is deoxyribonucleic acid.

38. The method of claim 37 in which the deoxyribonucleic acid is first extracted from the cell.

39. The method of claim 33 in which the hybridization is detected by an in situ hybridization method.

40. The method of claim 33 in which the hybridization is detected by a Northern blot method.

41. The method of claim 33 in which the polynucleotide of step (a) is used as a primer in an amplification method.

42. The method of claim 41 in which the method is polymerase chain reaction.

43. The method of claim 33 in which the cell is obtained from ovary.

44. The method of claim 33 in which the cell is obtained from prostate.

45. The method of claim 33 in which the cell is obtained from testis.

46. The method of claim 33 in which the cell is a sperm.

47. The method of claim 33 in which the cell is an ovum.

48. The method of claim 33 in which the cell is obtained from ovarian follicular fluids.

* * * * *

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
        (A) LENGTH: 2991 base pairs
        (B) TYPE: nucleic acid
        (C) STRANDEDNESS: single
        (D) TOPOLOGY: unknown (ii) MOLECULE TYPE: cDNA (ix) FEATURE:
        (A) NAME/KEY: CDS
        (B) LOCATION: 1..2991

(xi) SEQUENCE DESCRIPTION: SEQ ID NO:1:

```
GCG CGC GCG ACG CAG GTG CCC GAG CCC CGG CCC GCG CCC ATC TCT GCC      48
Ala Arg Ala Thr Gln Val Pro Glu Pro Arg Pro Ala Pro Ile Ser Ala
```

```
  1                    5                     10                    15
TTC GGT CGA GTT GGA CCC CCG GAT CAA GGT GTA CTT CTC TGA AGT AAG    96
Phe Gly Arg Val Gly Pro Pro Asp Gln Gly Val Leu Leu  *  Ser Lys
             20                  25                  30

ATG ATT TGT CAA AAA TTC TGT GTG GTT TTG TTA CAT TGG GAA TTT ATT   144
Met Ile Cys Gln Lys Phe Cys Val Val Leu Leu His Trp Glu Phe Ile
         35                  40                  45

TAT GTG ATA ACT GCG TTT AAC TTG TCA TAT CCA ATT ACT CCT TGG AGA   192
Tyr Val Ile Thr Ala Phe Asn Leu Ser Tyr Pro Ile Thr Pro Trp Arg
     50                  55                  60

TTT AAG TTG TCT TGC ATG CCA CCA AAT TCA ACC TAT GAC TAC TTC CTT   240
Phe Lys Leu Ser Cys Met Pro Pro Asn Ser Thr Tyr Asp Tyr Phe Leu
 65                  70                  75                  80

TTG CCT GCT GGA CTC TCA AAG AAT ACT TCA AAT TCG AAT GGA CAT TAT   288
Leu Pro Ala Gly Leu Ser Lys Asn Thr Ser Asn Ser Asn Gly His Tyr
                 85                  90                  95

GAG ACA GCT GTT GAA CCT AAG TTT AAT TCA AGT GGT ACT CAC TTT TCT   336
Glu Thr Ala Val Glu Pro Lys Phe Asn Ser Ser Gly Thr His Phe Ser
             100                 105                 110

AAC TTA TCC AAA GCA ACT TTC CAC TGT TGC TTT CGG AGT GAG CAA GAT   384
Asn Leu Ser Lys Ala Thr Phe His Cys Cys Phe Arg Ser Glu Gln Asp
         115                 120                 125

AGA AAC TGC TCC TTA TGT GCA GAC AAC ATT GAA GGA AGG ACA TTT GTT   432
Arg Asn Cys Ser Leu Cys Ala Asp Asn Ile Glu Gly Arg Thr Phe Val
     130                 135                 140

TCA ACA GTA AAT TCT TTA GTT TTT CAA CAA ATA GAT GCA AAC TGG AAC   480
Ser Thr Val Asn Ser Leu Val Phe Gln Gln Ile Asp Ala Asn Trp Asn
145                 150                 155                 160

ATA CAG TGC TGG CTA AAA GGA GAC TTA AAA TTA TTC ATC TGT TAT GTG   528
Ile Gln Cys Trp Leu Lys Gly Asp Leu Lys Leu Phe Ile Cys Tyr Val
                 165                 170                 175

GAG TCA TTA TTT AAG AAT CTA TTC AGG AAT TAT AAC TAT AAG GTC CAT   576
Glu Ser Leu Phe Lys Asn Leu Phe Arg Asn Tyr Asn Tyr Lys Val His
             180                 185                 190

CTT TTA TAT GTT CTG CCT GAA GTG TTA GAA GAT TCA CCT CTG GTT CCC   624
Leu Leu Tyr Val Leu Pro Glu Val Leu Glu Asp Ser Pro Leu Val Pro
         195                 200                 205

CAA AAA GGC AGT TTT CAG ATG GTT CAC TGC AAT TGC AGT GTT CAT GAA   672
Gln Lys Gly Ser Phe Gln Met Val His Cys Asn Cys Ser Val His Glu
     210                 215                 220

TGT TGT GAA TGT CTT GTG CCT GTG CCA ACA GCC AAA CTC AAC GAC ACT   720
Cys Cys Glu Cys Leu Val Pro Val Pro Thr Ala Lys Leu Asn Asp Thr
225                 230                 235                 240

CTC CTT ATG TGT TTG AAA ATC ACA TCT GGT GGA GTA ATT TTC CGG TCA   768
Leu Leu Met Cys Leu Lys Ile Thr Ser Gly Gly Val Ile Phe Arg Ser
                 245                 250                 255

CCT CTA ATG TCA GTT CAG CCC ATA AAT ATG GTG AAG CCT GAT CCA CCA   816
Pro Leu Met Ser Val Gln Pro Ile Asn Met Val Lys Pro Asp Pro Pro
             260                 265                 270

TTA GGT TTG CAT ATG GAA ATC ACA GAT GAT GGT AAT TTA AAG ATT TCT   864
Leu Gly Leu His Met Glu Ile Thr Asp Asp Gly Asn Leu Lys Ile Ser
         275                 280                 285

TGG TCC AGC CCA CCA TTG GTA CCA TTT CCA CTT CAA TAT CAA GTG AAA   912
Trp Ser Ser Pro Pro Leu Val Pro Phe Pro Leu Gln Tyr Gln Val Lys
     290                 295                 300

TAT TCA GAG AAT TCT ACA ACA GTT ATC AGA GAA GCT GAC AAG ATT GTC   960
Tyr Ser Glu Asn Ser Thr Thr Val Ile Arg Glu Ala Asp Lys Ile Val
305                 310                 315                 320

TCA GCT ACA TCC CTG CTA GTA GAC AGT ATA CTT CCT GGG TCT TCG TAT  1008
Ser Ala Thr Ser Leu Leu Val Asp Ser Ile Leu Pro Gly Ser Ser Tyr
```

```
                         325                 330                 335
GAG GTT CAG GTG AGG GGC AAG AGA CTG GAT GGC CCA GGA ATC TGG AGT            1056
Glu Val Gln Val Arg Gly Lys Arg Leu Asp Gly Pro Gly Ile Trp Ser
                340                 345                 350

GAC TGG AGT ACT CCT CGT GTC TTT ACC ACA CAA GAT GTC ATA TAC TTT            1104
Asp Trp Ser Thr Pro Arg Val Phe Thr Thr Gln Asp Val Ile Tyr Phe
                355                 360                 365

CCA CCT AAA ATT CTG ACA AGT GTT GGG TCT AAT GTT TCT TTT CAC TGC            1152
Pro Pro Lys Ile Leu Thr Ser Val Gly Ser Asn Val Ser Phe His Cys
            370                 375                 380

ATC TAT AAG AAG GAA AAC AAG ATT GTT CCC TCA AAA GAG ATT GTT TGG            1200
Ile Tyr Lys Lys Glu Asn Lys Ile Val Pro Ser Lys Glu Ile Val Trp
385                 390                 395                 400

TGG ATG AAT TTA GCT GAG AAA ATT CCT CAA AGC CAG TAT GAT GTT GTG            1248
Trp Met Asn Leu Ala Glu Lys Ile Pro Gln Ser Gln Tyr Asp Val Val
                405                 410                 415

AGT GAT CAT GTT AGC AAA GTT ACT TTT TTC AAT CTG AAT GAA ACC AAA            1296
Ser Asp His Val Ser Lys Val Thr Phe Phe Asn Leu Asn Glu Thr Lys
                420                 425                 430

CCT CGA GGA AAG TTT ACC TAT GAT GCA GTG TAC TGC TGC AAT GAA CAT            1344
Pro Arg Gly Lys Phe Thr Tyr Asp Ala Val Tyr Cys Cys Asn Glu His
                435                 440                 445

GAA TGC CAT CAT CGC TAT GCT GAA TTA TAT GTG ATT GAT GTC AAT ATC            1392
Glu Cys His His Arg Tyr Ala Glu Leu Tyr Val Ile Asp Val Asn Ile
450                 455                 460

AAT ATC TCA TGT GAA ACT GAT GGG TAC TTA ACT AAA ATG ACT TGC AGA            1440
Asn Ile Ser Cys Glu Thr Asp Gly Tyr Leu Thr Lys Met Thr Cys Arg
465                 470                 475                 480

TGG TCA ACC AGT ACA ATC CAG TCA CTT GCG GAA AGC ACT TTG CAA TTG            1488
Trp Ser Thr Ser Thr Ile Gln Ser Leu Ala Glu Ser Thr Leu Gln Leu
                485                 490                 495

AGG TAT CAT AGG AGC AGC CTT TAC TGT TCT GAT ATT CCA TCT ATT CAT            1536
Arg Tyr His Arg Ser Ser Leu Tyr Cys Ser Asp Ile Pro Ser Ile His
                500                 505                 510

CCC ATA TCT GAG CCC AAA GAT TGC TAT TTG CAG AGT GAT GGT TTT TAT            1584
Pro Ile Ser Glu Pro Lys Asp Cys Tyr Leu Gln Ser Asp Gly Phe Tyr
            515                 520                 525

GAA TGC ATT TTC CAG CCA ATC TTC CTA TTA TCT GGC TAC ACA ATG TGG            1632
Glu Cys Ile Phe Gln Pro Ile Phe Leu Leu Ser Gly Tyr Thr Met Trp
        530                 535                 540

ATT AGG ATC AAT CAC TCT CTA GGT TCA CTT GAC TCT CCA CCA ACA TGT            1680
Ile Arg Ile Asn His Ser Leu Gly Ser Leu Asp Ser Pro Pro Thr Cys
545                 550                 555                 560

GTC CTT CCT GAT TCT GTG GTG AAG CCA CTG CCT CCA TCC AGT GTG AAA            1728
Val Leu Pro Asp Ser Val Val Lys Pro Leu Pro Pro Ser Ser Val Lys
                565                 570                 575

GCA GAA ATT ACT ATA AAC ATT GGA TTA TTG AAA ATA TCT TGG GAA AAG            1776
Ala Glu Ile Thr Ile Asn Ile Gly Leu Leu Lys Ile Ser Trp Glu Lys
                580                 585                 590

CCA GTC TTT CCA GAG AAT AAC CTT CAA TTC CAG ATT CGC TAT GGT TTA            1824
Pro Val Phe Pro Glu Asn Asn Leu Gln Phe Gln Ile Arg Tyr Gly Leu
                595                 600                 605

AGT GGA AAA GAA GTA CAA TGG AAG ATG TAT GAG GTT TAT GAT GCA AAA            1872
Ser Gly Lys Glu Val Gln Trp Lys Met Tyr Glu Val Tyr Asp Ala Lys
            610                 615                 620

TCA AAA TCT GTC AGT CTC CCA GTT CCA GAC TTG TGT GCA GTC TAT GCT            1920
Ser Lys Ser Val Ser Leu Pro Val Pro Asp Leu Cys Ala Val Tyr Ala
625                 630                 635                 640

GTT CAG GTG CGC TGT AAG AGG CTA GAT GGA CTG GGA TAT TGG AGT AAT            1968
Val Gln Val Arg Cys Lys Arg Leu Asp Gly Leu Gly Tyr Trp Ser Asn
```

-continued

```
                       645                     650                     655
TGG AGC AAT CCA GCC TAC ACA GTT GTC ATG GAT ATA AAA GTT CCT ATG                    2016
Trp Ser Asn Pro Ala Tyr Thr Val Val Met Asp Ile Lys Val Pro Met
            660                     665                     670

AGA GGA CCT GAA TTT TGG AGA ATA ATT AAT GGA GAT ACT ATG AAA AAG                    2064
Arg Gly Pro Glu Phe Trp Arg Ile Ile Asn Gly Asp Thr Met Lys Lys
        675                     680                     685

GAG AAA AAT GTC ACT TTA CTT TGG AAG CCC CTG ATG AAA AAT GAC TCA                    2112
Glu Lys Asn Val Thr Leu Leu Trp Lys Pro Leu Met Lys Asn Asp Ser
        690                     695                     700

TTG TGC AGT GTT CAG AGA TAT GTG ATA AAC CAT CAT ACT TCC TGC AAT                    2160
Leu Cys Ser Val Gln Arg Tyr Val Ile Asn His His Thr Ser Cys Asn
705                     710                     715                     720

GGA ACA TGG TCA GAA GAT GTG GGA AAT CAC ACG AAA TTC ACT TTC CTG                    2208
Gly Thr Trp Ser Glu Asp Val Gly Asn His Thr Lys Phe Thr Phe Leu
                725                     730                     735

TGG ACA GAG CAA GCA CAT ACT GTT ACG GTT CTG GCC ATC AAT TCA ATT                    2256
Trp Thr Glu Gln Ala His Thr Val Thr Val Leu Ala Ile Asn Ser Ile
                740                     745                     750

GGT GCT TCT GTT GCA AAT TTT AAT TTA ACC TTT TCA TGG CCT ATG AGC                    2304
Gly Ala Ser Val Ala Asn Phe Asn Leu Thr Phe Ser Trp Pro Met Ser
            755                     760                     765

AAA GTA AAT ATC GTG CAG TCA CTC AGT GCT TAT CCT TTA AAC AGC AGT                    2352
Lys Val Asn Ile Val Gln Ser Leu Ser Ala Tyr Pro Leu Asn Ser Ser
        770                     775                     780

TGT GTG ATT GTT TCC TGG ATA CTA TCA CCC AGT GAT TAC AAG CTA ATG                    2400
Cys Val Ile Val Ser Trp Ile Leu Ser Pro Ser Asp Tyr Lys Leu Met
785                     790                     795                     800

TAT TTT ATT ATT GAG TGG AAA AAT CTT AAT GAA GAT GGT GAA ATA AAA                    2448
Tyr Phe Ile Ile Glu Trp Lys Asn Leu Asn Glu Asp Gly Glu Ile Lys
                805                     810                     815

TGG CTT AGA ATC TCT TCA TCT GTT AAG AAG TAT TAT ATC CAT GAT CAT                    2496
Trp Leu Arg Ile Ser Ser Ser Val Lys Lys Tyr Tyr Ile His Asp His
                820                     825                     830

TTT ATC CCC ATT GAG AAG TAC CAG TTC AGT CTT TAC CCA ATA TTT ATG                    2544
Phe Ile Pro Ile Glu Lys Tyr Gln Phe Ser Leu Tyr Pro Ile Phe Met
            835                     840                     845

GAA GGA GTG GGA AAA CCA AAG ATA ATT AAT AGT TTC ACT CAA GAT GAT                    2592
Glu Gly Val Gly Lys Pro Lys Ile Ile Asn Ser Phe Thr Gln Asp Asp
        850                     855                     860

ATT GAA AAA CAC CAG AGT GAT GCA GGT TTA TAT GTA ATT GTG CCA GTA                    2640
Ile Glu Lys His Gln Ser Asp Ala Gly Leu Tyr Val Ile Val Pro Val
865                     870                     875                     880

ATT ATT TCC TCT TCC ATC TTA TTG CTT GGA ACA TTA TTA ATA TCA CAC                    2688
Ile Ile Ser Ser Ser Ile Leu Leu Leu Gly Thr Leu Leu Ile Ser His
                885                     890                     895

CAA AGA ATG AAA AAG CTA TTT TGG GAA GAT GTT CCG AAC CCC AAG AAT                    2736
Gln Arg Met Lys Lys Leu Phe Trp Glu Asp Val Pro Asn Pro Lys Asn
                900                     905                     910

TGT TCC TGG GCA CAA GGA CTT AAT TTT CAG AAG ATG CTT GAA GGC AGC                    2784
Cys Ser Trp Ala Gln Gly Leu Asn Phe Gln Lys Met Leu Glu Gly Ser
            915                     920                     925

ATG TTC GTT AAG AGT CAT CAC CAC TCC CTA ATC TCA AGT ACC CAG GGA                    2832
Met Phe Val Lys Ser His His His Ser Leu Ile Ser Ser Thr Gln Gly
        930                     935                     940

CAC AAA CAC TGC GGA AGG CCA CAG GGT CCT CTG CAT AGG AAA ACC AGA                    2880
His Lys His Cys Gly Arg Pro Gln Gly Pro Leu His Arg Lys Thr Arg
945                     950                     955                     960

GAC CTT TGT TCA CTT GTT TAT CTG CTG ACC CTC CCT CCA CTA TTG TCC                    2928
Asp Leu Cys Ser Leu Val Tyr Leu Leu Thr Leu Pro Pro Leu Leu Ser
```

965                970                975
TAT GAC CCT GCC AAA TCC CCC TCT GTG AGA AAC ACC CAA GAA TGA TCA         2976
Tyr Asp Pro Ala Lys Ser Pro Ser Val Arg Asn Thr Gln Glu *   Ser
                980                 985                 990

ATA AAA AAA AAA AAA                                                      2991
Ile Lys Lys Lys Lys
        995

(2) INFORMATION FOR SEQ ID NO:2:

(i) SEQUENCE CHARACTERISTICS:
        (A) LENGTH: 29 amino acids
        (B) TYPE: amino acid
        (D) TOPOLOGY: linear (ii) MOLECULE TYPE: protein (xi) SEQUENCE DESCRIPTION: SEQ ID NO:2:

Ala Arg Ala Thr Gln Val Pro Glu Pro Arg Pro Ala Pro Ile Ser Ala
 1               5                  10                  15

Phe Gly Arg Val Gly Pro Pro Asp Gln Gly Val Leu Leu
                20                  25

(2) INFORMATION FOR SEQ ID NO:3:

(i) SEQUENCE CHARACTERISTICS:
        (A) LENGTH: 960 amino acids
        (B) TYPE: amino acid
        (D) TOPOLOGY: linear (ii) MOLECULE TYPE: protein (xi) SEQUENCE DESCRIPTION: SEQ ID NO:3:

Ser Lys Met Ile Cys Gln Lys Phe Cys Val Val Leu Leu His Trp Glu
 1               5                  10                  15

Phe Ile Tyr Val Ile Thr Ala Phe Asn Leu Ser Tyr Pro Ile Thr Pro
                20                  25                  30

Trp Arg Phe Lys Leu Ser Cys Met Pro Pro Asn Ser Thr Tyr Asp Tyr
            35                  40                  45

Phe Leu Leu Pro Ala Gly Leu Ser Lys Asn Thr Ser Asn Ser Asn Gly
    50                  55                  60

His Tyr Glu Thr Ala Val Glu Pro Lys Phe Asn Ser Ser Gly Thr His
65                  70                  75                  80

Phe Ser Asn Leu Ser Lys Ala Thr Phe His Cys Cys Phe Arg Ser Glu
                85                  90                  95

Gln Asp Arg Asn Cys Ser Leu Cys Ala Asp Asn Ile Glu Gly Arg Thr
            100                 105                 110

Phe Val Ser Thr Val Asn Ser Leu Val Phe Gln Gln Ile Asp Ala Asn
    115                 120                 125

Trp Asn Ile Gln Cys Trp Leu Lys Gly Asp Leu Lys Leu Phe Ile Cys
130                 135                 140

Tyr Val Glu Ser Leu Phe Lys Asn Leu Phe Arg Asn Tyr Asn Tyr Lys
145                 150                 155                 160

Val His Leu Leu Tyr Val Leu Pro Glu Val Leu Glu Asp Ser Pro Leu
                165                 170                 175

Val Pro Gln Lys Gly Ser Phe Gln Met Val His Cys Asn Cys Ser Val
            180                 185                 190

His Glu Cys Cys Glu Cys Leu Val Pro Val Pro Thr Ala Lys Leu Asn
    195                 200                 205

Asp Thr Leu Leu Met Cys Leu Lys Ile Thr Ser Gly Gly Val Ile Phe

-continued

```
            210                 215                 220
Arg Ser Pro Leu Met Ser Val Gln Pro Ile Asn Met Val Lys Pro Asp
225                 230                 235                 240

Pro Pro Leu Gly Leu His Met Glu Ile Thr Asp Asp Gly Asn Leu Lys
                    245                 250                 255

Ile Ser Trp Ser Ser Pro Pro Leu Val Pro Phe Pro Leu Gln Tyr Gln
                260                 265                 270

Val Lys Tyr Ser Glu Asn Ser Thr Thr Val Ile Arg Glu Ala Asp Lys
            275                 280                 285

Ile Val Ser Ala Thr Ser Leu Leu Val Asp Ser Ile Leu Pro Gly Ser
290                 295                 300

Ser Tyr Glu Val Gln Val Arg Gly Lys Arg Leu Asp Gly Pro Gly Ile
305                 310                 315                 320

Trp Ser Asp Trp Ser Thr Pro Arg Val Phe Thr Thr Gln Asp Val Ile
                325                 330                 335

Tyr Phe Pro Pro Lys Ile Leu Thr Ser Val Gly Ser Asn Val Ser Phe
                340                 345                 350

His Cys Ile Tyr Lys Lys Glu Asn Lys Ile Val Pro Ser Lys Glu Ile
                355                 360                 365

Val Trp Trp Met Asn Leu Ala Glu Lys Ile Pro Gln Ser Gln Tyr Asp
370                 375                 380

Val Val Ser Asp His Val Ser Lys Val Thr Phe Phe Asn Leu Asn Glu
385                 390                 395                 400

Thr Lys Pro Arg Gly Lys Phe Thr Tyr Asp Ala Val Tyr Cys Cys Asn
                405                 410                 415

Glu His Glu Cys His His Arg Tyr Ala Glu Leu Tyr Val Ile Asp Val
                420                 425                 430

Asn Ile Asn Ile Ser Cys Glu Thr Asp Gly Tyr Leu Thr Lys Met Thr
                435                 440                 445

Cys Arg Trp Ser Thr Ser Thr Ile Gln Ser Leu Ala Glu Ser Thr Leu
450                 455                 460

Gln Leu Arg Tyr His Arg Ser Ser Leu Tyr Cys Ser Asp Ile Pro Ser
465                 470                 475                 480

Ile His Pro Ile Ser Glu Pro Lys Asp Cys Tyr Leu Gln Ser Asp Gly
                485                 490                 495

Phe Tyr Glu Cys Ile Phe Gln Pro Ile Phe Leu Leu Ser Gly Tyr Thr
                500                 505                 510

Met Trp Ile Arg Ile Asn His Ser Leu Gly Ser Leu Asp Ser Pro Pro
                515                 520                 525

Thr Cys Val Leu Pro Asp Ser Val Val Lys Pro Leu Pro Pro Ser Ser
530                 535                 540

Val Lys Ala Glu Ile Thr Ile Asn Ile Gly Leu Leu Lys Ile Ser Trp
545                 550                 555                 560

Glu Lys Pro Val Phe Pro Glu Asn Asn Leu Gln Phe Gln Ile Arg Tyr
                565                 570                 575

Gly Leu Ser Gly Lys Glu Val Gln Trp Lys Met Tyr Glu Val Tyr Asp
                580                 585                 590

Ala Lys Ser Lys Ser Val Ser Leu Pro Val Pro Asp Leu Cys Ala Val
                595                 600                 605

Tyr Ala Val Gln Val Arg Cys Lys Arg Leu Asp Gly Leu Gly Tyr Trp
                610                 615                 620

Ser Asn Trp Ser Asn Pro Ala Tyr Thr Val Val Met Asp Ile Lys Val
625                 630                 635                 640
```

| | | | | | | | | | | | |
|---|---|---|---|---|---|---|---|---|---|---|---|
|Pro|Met|Arg|Gly|Pro|Glu|Phe|Trp|Arg|Ile|Ile|Asn|Gly|Asp|Thr|Met|

```
Pro Met Arg Gly Pro Glu Phe Trp Arg Ile Ile Asn Gly Asp Thr Met
                645                 650                 655

Lys Lys Glu Lys Asn Val Thr Leu Leu Trp Lys Pro Leu Met Lys Asn
                660                 665                 670

Asp Ser Leu Cys Ser Val Gln Arg Tyr Val Ile Asn His His Thr Ser
                675                 680                 685

Cys Asn Gly Thr Trp Ser Glu Asp Val Gly Asn His Thr Lys Phe Thr
        690                 695                 700

Phe Leu Trp Thr Glu Gln Ala His Thr Val Thr Val Leu Ala Ile Asn
705                 710                 715                 720

Ser Ile Gly Ala Ser Val Ala Asn Phe Asn Leu Thr Phe Ser Trp Pro
                725                 730                 735

Met Ser Lys Val Asn Ile Val Gln Ser Leu Ser Ala Tyr Pro Leu Asn
                740                 745                 750

Ser Ser Cys Val Ile Val Ser Trp Ile Leu Ser Pro Ser Asp Tyr Lys
            755                 760                 765

Leu Met Tyr Phe Ile Ile Glu Trp Lys Asn Leu Asn Glu Asp Gly Glu
            770                 775                 780

Ile Lys Trp Leu Arg Ile Ser Ser Ser Val Lys Lys Tyr Tyr Ile His
785                 790                 795                 800

Asp His Phe Ile Pro Ile Glu Lys Tyr Gln Phe Ser Leu Tyr Pro Ile
                805                 810                 815

Phe Met Glu Gly Val Gly Lys Pro Lys Ile Ile Asn Ser Phe Thr Gln
                820                 825                 830

Asp Asp Ile Glu Lys His Gln Ser Asp Ala Gly Leu Tyr Val Ile Val
                835                 840                 845

Pro Val Ile Ile Ser Ser Ser Ile Leu Leu Leu Gly Thr Leu Leu Ile
                850                 855                 860

Ser His Gln Arg Met Lys Lys Leu Phe Trp Glu Asp Val Pro Asn Pro
865                 870                 875                 880

Lys Asn Cys Ser Trp Ala Gln Gly Leu Asn Phe Gln Lys Met Leu Glu
                885                 890                 895

Gly Ser Met Phe Val Lys Ser His His His Ser Leu Ile Ser Ser Thr
                900                 905                 910

Gln Gly His Lys His Cys Gly Arg Pro Gln Gly Pro Leu His Arg Lys
                915                 920                 925

Thr Arg Asp Leu Cys Ser Leu Val Tyr Leu Leu Thr Leu Pro Pro Leu
930                 935                 940

Leu Ser Tyr Asp Pro Ala Lys Ser Pro Ser Val Arg Asn Thr Gln Glu
945                 950                 955                 960

(2) INFORMATION FOR SEQ ID NO:4:

(i) SEQUENCE CHARACTERISTICS:
        (A) LENGTH: 6 amino acids
        (B) TYPE: amino acid
        (D) TOPOLOGY: linear (ii) MOLECULE TYPE: protein (xi) SEQUENCE DESCRIPTION: SEQ ID NO:4:

Ser Ile Lys Lys Lys Lys
 1               5

(2) INFORMATION FOR SEQ ID NO:5:

(i) SEQUENCE CHARACTERISTICS:
        (A) LENGTH: 241 base pairs
```

(B) TYPE: nucleic acid
        (C) STRANDEDNESS: single
        (D) TOPOLOGY: unknown (ii) MOLECULE TYPE: cDNA (xi) SEQUENCE DESCRIPTION: SEQ ID NO:5:

AGGACTTAAT TTTCAGAAGA TGCTTGAAGG CAGCATGTTC GTTAAGAGTC ATCACCACTC    60

CCTAATCTCA AGTACCCAGG GACACAAACA CTGCGGAAGG CCACAGGGTC CTCTGCATAG    120

GAAAACCAGA GACCTTTGTT CACTTGTTTA TCTGCTGACC CTCCCTCCAC TATTGTCCTA    180

TGACCCTGCC AAATCCCCCT CTGTGAGAAA CACCCAAGAA TGATCAATAA AAAAAAAAAA    240

A                                                                    241

(2) INFORMATION FOR SEQ ID NO:6:

(i) SEQUENCE CHARACTERISTICS:
        (A) LENGTH: 130 base pairs
        (B) TYPE: nucleic acid
        (C) STRANDEDNESS: single
        (D) TOPOLOGY: unknown (ii) MOLECULE TYPE: cDNA (xi) SEQUENCE DESCRIPTION: SEQ ID NO:6:

AGGACTTAAT TTTCAGAAGA AAATGCCTGG CACAAAGGAA CTACTGGGTG GAGGTTGGTT    60

GACTTAGGAA ATGCTTGTGA AGCTACGTCC TACCTCGTGC GCACCTGCTC TCCCTGAGGT    120

GTGCACAATG                                                           130

(2) INFORMATION FOR SEQ ID NO:7:

(i) SEQUENCE CHARACTERISTICS:
        (A) LENGTH: 127 base pairs
        (B) TYPE: nucleic acid
        (C) STRANDEDNESS: single
        (D) TOPOLOGY: unknown (ii) MOLECULE TYPE: cDNA (xi) SEQUENCE DESCRIPTION: SEQ ID NO:7:

AGGACTTAAT TTTCAGAAGA GAACGGACAT TCTTTGAAGT CTAATCATGA TCACTACAGA    60

TGAACCCAAT GTGCCAACTT CCCAACAGTC TATAGAGTAT TAGAAGATTT TTACATTCTG    120

AAGAAGG                                                              127

(2) INFORMATION FOR SEQ ID NO:8:

(i) SEQUENCE CHARACTERISTICS:
        (A) LENGTH: 958 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:8:

Met Ile Cys Gln Lys Phe Cys Val Val Leu His Trp Glu Phe Ile
1               5                   10                  15

Tyr Val Ile Thr Ala Phe Asn Leu Ser Tyr Pro Ile Thr Pro Trp Arg
            20                  25                  30

Phe Lys Leu Ser Cys Met Pro Pro Asn Ser Thr Tyr Asp Tyr Phe Leu
        35                  40                  45

Leu Pro Ala Gly Leu Ser Lys Asn Thr Ser Asn Ser Asn Gly His Tyr
    50                  55                  60

```
Glu Thr Ala Val Glu Pro Lys Phe Asn Ser Ser Gly Thr His Phe Ser
 65                  70                  75                  80

Asn Leu Ser Lys Ala Thr Phe His Cys Cys Phe Arg Ser Glu Gln Asp
                 85                  90                  95

Arg Asn Cys Ser Leu Cys Ala Asp Asn Ile Glu Gly Arg Thr Phe Val
            100                 105                 110

Ser Thr Val Asn Ser Leu Val Phe Gln Gln Ile Asp Ala Asn Trp Asn
            115                 120                 125

Ile Gln Cys Trp Leu Lys Gly Asp Leu Lys Leu Phe Ile Cys Tyr Val
        130                 135                 140

Glu Ser Leu Phe Lys Asn Leu Phe Arg Asn Tyr Asn Lys Val His
145                 150                 155                 160

Leu Leu Tyr Val Leu Pro Glu Val Leu Glu Asp Ser Pro Leu Val Pro
                165                 170                 175

Gln Lys Gly Ser Phe Gln Met Val His Cys Asn Cys Ser Val His Glu
            180                 185                 190

Cys Cys Glu Cys Leu Val Pro Val Pro Thr Ala Lys Leu Asn Asp Thr
        195                 200                 205

Leu Leu Met Cys Leu Lys Ile Thr Ser Gly Gly Val Ile Phe Arg Ser
210                 215                 220

Pro Leu Met Ser Val Gln Pro Ile Asn Met Val Lys Pro Asp Pro Pro
225                 230                 235                 240

Leu Gly Leu His Met Glu Thr Thr Asp Asp Gly Asn Leu Lys Ile Ser
                245                 250                 255

Trp Ser Ser Pro Pro Leu Val Pro Phe Pro Leu Gln Tyr Gln Val Lys
            260                 265                 270

Tyr Ser Glu Asn Ser Thr Thr Val Thr Arg Glu Ala Asp Lys Ile Val
            275                 280                 285

Ser Ala Thr Ser Leu Leu Val Asp Ser Ile Leu Pro Gly Ser Ser Tyr
        290                 295                 300

Glu Val Gln Val Arg Gly Lys Arg Leu Asp Gly Pro Gly Ile Trp Ser
305                 310                 315                 320

Asp Trp Ser Thr Pro Arg Val Phe Thr Thr Gln Asp Val Ile Tyr Phe
                325                 330                 335

Pro Pro Lys Ile Leu Thr Ser Val Gly Ser Asn Val Ser Phe His Cys
            340                 345                 350

Ile Tyr Lys Lys Glu Asn Lys Ile Val Pro Ser Lys Glu Ile Val Trp
        355                 360                 365

Trp Met Asn Leu Ala Glu Lys Ile Pro Gln Ser Gln Tyr Asp Val Val
    370                 375                 380

Ser Asp His Val Ser Lys Val Thr Phe Phe Asn Leu Asn Glu Thr Lys
385                 390                 395                 400

Pro Arg Gly Lys Phe Thr Tyr Asp Ala Val Tyr Cys Cys Asn Glu His
                405                 410                 415

Glu Cys His His Arg Tyr Ala Glu Leu Tyr Val Ile Asp Val Asn Ile
            420                 425                 430

Asn Ile Ser Cys Glu Thr Asp Gly Tyr Leu Thr Lys Met Thr Cys Arg
        435                 440                 445

Trp Ser Thr Ser Thr Ile Gln Ser Leu Ala Glu Ser Thr Leu Gln Leu
    450                 455                 460

Arg Tyr His Arg Ser Ser Leu Tyr Cys Ser Asp Ile Pro Ser Ile His
465                 470                 475                 480

Pro Ile Ser Glu Pro Lys Asp Cys Tyr Leu Gln Ser Asp Gly Phe Tyr
```

-continued

```
                  485                 490                 495
Glu Cys Ile Phe Gln Pro Ile Phe Leu Leu Ser Gly Tyr Thr Met Trp
                500                 505                 510

Ile Arg Ile Asn His Ser Leu Gly Ser Leu Asp Ser Pro Pro Thr Cys
            515                 520                 525

Val Leu Pro Asp Ser Val Val Lys Pro Leu Pro Pro Ser Ser Val Lys
        530                 535                 540

Ala Glu Ile Thr Ile Asn Thr Gly Leu Leu Lys Ile Ser Trp Glu Lys
545                 550                 555                 560

Pro Val Phe Pro Glu Asn Asn Leu Gln Phe Gln Ile Arg Tyr Gly Leu
                565                 570                 575

Ser Gly Lys Glu Val Gln Trp Lys Met Tyr Glu Val Tyr Asp Ala Lys
            580                 585                 590

Ser Lys Ser Val Ser Leu Pro Val Pro Asp Leu Ala Cys Val Tyr Ala
        595                 600                 605

Val Gln Val Arg Cys Lys Arg Leu Asp Gly Leu Gly Tyr Trp Ser Asn
        610                 615                 620

Trp Ser Asn Pro Ala Tyr Thr Val Met Asp Ile Lys Val Pro Met
625                 630                 635                 640

Arg Gly Pro Glu Phe Trp Arg Ile Ile Asn Gly Asp Thr Met Lys Lys
                645                 650                 655

Glu Lys Asn Val Thr Leu Leu Trp Lys Pro Leu Met Lys Asn Asp Ser
            660                 665                 670

Leu Cys Ser Val Gln Arg Tyr Val Ile Asn His His Thr Ser Cys Asn
        675                 680                 685

Gly Thr Trp Ser Glu Asp Val Gly Asn His Thr Lys Phe Thr Phe Leu
        690                 695                 700

Trp Thr Glu Gln Ala His Thr Val Thr Val Leu Ala Ile Asn Ser Ile
705                 710                 715                 720

Gly Ala Ser Val Ala Asn Phe Asn Leu Thr Phe Ser Trp Pro Met Ser
                725                 730                 735

Lys Val Asn Ile Val Gln Ser Leu Ser Ala Tyr Pro Leu Asn Ser Ser
            740                 745                 750

Cys Val Ile Val Ser Trp Ile Leu Ser Pro Ser Asp Tyr Lys Leu Met
        755                 760                 765

Tyr Phe Ile Ile Glu Trp Lys Asn Leu Asn Glu Asp Gly Glu Ile Lys
        770                 775                 780

Trp Leu Arg Ile Ser Ser Ser Val Lys Lys Tyr Tyr Ile His Asp His
785                 790                 795                 800

Phe Ile Pro Ile Glu Lys Tyr Gln Phe Ser Leu Tyr Pro Ile Phe Met
                805                 810                 815

Glu Gly Val Gly Lys Pro Lys Ile Ile Asn Ser Phe Thr Gln Asp Asp
            820                 825                 830

Ile Glu Lys His Gln Ser Asp Ala Gly Leu Tyr Val Ile Val Pro Val
        835                 840                 845

Ile Ile Ser Ser Ser Ile Leu Leu Leu Gly Thr Leu Leu Ile Ser His
        850                 855                 860

Gln Arg Met Lys Lys Leu Phe Trp Glu Asp Val Pro Asn Pro Lys Asn
865                 870                 875                 880

Cys Ser Trp Ala Gln Gly Leu Asn Phe Gln Lys Met Leu Glu Gly Ser
                885                 890                 895

Met Phe Val Lys Ser His His Ser Leu Ile Ser Ser Thr Gln Gly
            900                 905                 910
```

```
His Lys His Cys Gly Arg Pro Gln Gly Pro Leu His Arg Lys Thr Arg
            915                 920                 925

Asp Leu Cys Ser Leu Val Tyr Leu Leu Thr Leu Pro Pro Leu Leu Ser
            930                 935                 940

Tyr Asp Pro Ala Lys Ser Pro Ser Val Arg Asn Thr Gln Glu
945                 950                 955

(2) INFORMATION FOR SEQ ID NO:9:

(i) SEQUENCE CHARACTERISTICS:
        (A) LENGTH: 906 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:9:

Met Ile Cys Gln Lys Phe Cys Val Val Leu Leu His Trp Glu Phe Ile
1               5                   10                  15

Tyr Val Ile Thr Ala Phe Asn Leu Ser Tyr Pro Ile Thr Pro Trp Arg
            20                  25                  30

Phe Lys Leu Ser Cys Met Pro Pro Asn Ser Thr Tyr Asp Tyr Phe Leu
            35                  40                  45

Leu Pro Ala Gly Leu Ser Lys Asn Thr Ser Asn Ser Asn Gly His Tyr
50                  55                  60

Glu Thr Ala Val Glu Pro Lys Phe Asn Ser Ser Gly Thr His Phe Ser
65                  70                  75                  80

Asn Leu Ser Lys Ala Thr Phe His Cys Cys Phe Arg Ser Glu Gln Asp
            85                  90                  95

Arg Asn Cys Ser Leu Cys Ala Asp Asn Ile Glu Gly Arg Thr Phe Val
            100                 105                 110

Ser Thr Val Asn Ser Leu Val Phe Gln Gln Ile Asp Ala Asn Trp Asn
            115                 120                 125

Ile Gln Cys Trp Leu Lys Gly Asp Leu Lys Leu Phe Ile Cys Tyr Val
            130                 135                 140

Glu Ser Leu Phe Lys Asn Leu Phe Arg Asn Tyr Asn Tyr Lys Val His
145                 150                 155                 160

Leu Leu Tyr Val Leu Pro Glu Val Leu Glu Asp Ser Pro Leu Val Pro
            165                 170                 175

Gln Lys Gly Ser Phe Gln Met Val His Cys Asn Cys Ser Val His Glu
            180                 185                 190

Cys Cys Glu Cys Leu Val Pro Val Pro Thr Ala Lys Leu Asn Asp Thr
            195                 200                 205

Leu Leu Met Cys Leu Lys Ile Thr Ser Gly Gly Val Ile Phe Arg Ser
210                 215                 220

Pro Leu Met Ser Val Gln Pro Ile Asn Met Val Lys Pro Asp Pro Pro
225                 230                 235                 240

Leu Gly Leu His Met Glu Thr Thr Asp Asp Gly Asn Leu Lys Ile Ser
            245                 250                 255

Trp Ser Ser Pro Pro Leu Val Pro Phe Pro Leu Gln Tyr Gln Val Lys
            260                 265                 270

Tyr Ser Glu Asn Ser Thr Thr Val Thr Arg Glu Ala Asp Lys Ile Val
            275                 280                 285

Ser Ala Thr Ser Leu Leu Val Asp Ser Ile Leu Pro Gly Ser Ser Tyr
            290                 295                 300

Glu Val Gln Val Arg Gly Lys Arg Leu Asp Gly Pro Gly Ile Trp Ser
```

-continued

```
              305                 310                 315                 320
Asp Trp Ser Thr Pro Arg Val Phe Thr Thr Gln Asp Val Ile Tyr Phe
                    325                 330                 335
Pro Pro Lys Ile Leu Thr Ser Val Gly Ser Asn Val Ser Phe His Cys
                340                 345                 350
Ile Tyr Lys Lys Glu Asn Lys Ile Val Pro Ser Lys Glu Ile Val Trp
                355                 360                 365
Trp Met Asn Leu Ala Glu Lys Ile Pro Gln Ser Gln Tyr Asp Val Val
        370                 375                 380
Ser Asp His Val Ser Lys Val Thr Phe Phe Asn Leu Asn Glu Thr Lys
385                 390                 395                 400
Pro Arg Gly Lys Phe Thr Tyr Asp Ala Val Tyr Cys Cys Asn Glu His
                    405                 410                 415
Glu Cys His His Arg Tyr Ala Glu Leu Tyr Val Ile Asp Val Asn Ile
                420                 425                 430
Asn Ile Ser Cys Glu Thr Asp Gly Tyr Leu Thr Lys Met Thr Cys Arg
            435                 440                 445
Trp Ser Thr Ser Thr Ile Gln Ser Leu Ala Glu Ser Thr Leu Gln Leu
        450                 455                 460
Arg Tyr His Arg Ser Ser Leu Tyr Cys Ser Asp Ile Pro Ser Ile His
465                 470                 475                 480
Pro Ile Ser Glu Pro Lys Asp Cys Tyr Leu Gln Ser Asp Gly Phe Tyr
                    485                 490                 495
Glu Cys Ile Phe Gln Pro Ile Phe Leu Leu Ser Gly Tyr Thr Met Trp
                500                 505                 510
Ile Arg Ile Asn His Ser Leu Gly Ser Leu Asp Ser Pro Pro Thr Cys
            515                 520                 525
Val Leu Pro Asp Ser Val Val Lys Pro Leu Pro Pro Ser Ser Val Lys
        530                 535                 540
Ala Glu Ile Thr Ile Asn Thr Gly Leu Leu Lys Ile Ser Trp Glu Lys
545                 550                 555                 560
Pro Val Phe Pro Glu Asn Asn Leu Gln Phe Gln Ile Arg Tyr Gly Leu
                    565                 570                 575
Ser Gly Lys Glu Val Gln Trp Lys Met Tyr Glu Val Tyr Asp Ala Lys
                580                 585                 590
Ser Lys Ser Val Ser Leu Pro Val Pro Asp Leu Ala Cys Val Tyr Ala
            595                 600                 605
Val Gln Val Arg Cys Lys Arg Leu Asp Gly Leu Gly Tyr Trp Ser Asn
        610                 615                 620
Trp Ser Asn Pro Ala Tyr Thr Val Val Met Asp Ile Lys Val Pro Met
625                 630                 635                 640
Arg Gly Pro Glu Phe Trp Arg Ile Ile Asn Gly Asp Thr Met Lys Lys
                    645                 650                 655
Glu Lys Asn Val Thr Leu Leu Trp Lys Pro Leu Met Lys Asn Asp Ser
                660                 665                 670
Leu Cys Ser Val Gln Arg Tyr Val Ile Asn His His Thr Ser Cys Asn
            675                 680                 685
Gly Thr Trp Ser Glu Asp Val Gly Asn His Thr Lys Phe Thr Phe Leu
        690                 695                 700
Trp Thr Glu Gln Ala His Thr Val Thr Val Leu Ala Ile Asn Ser Ile
705                 710                 715                 720
Gly Ala Ser Val Ala Asn Phe Asn Leu Thr Phe Ser Trp Pro Met Ser
                    725                 730                 735
```

```
Lys Val Asn Ile Val Gln Ser Leu Ser Ala Tyr Pro Leu Asn Ser Ser
                740                 745                 750

Cys Val Ile Val Ser Trp Ile Leu Ser Pro Ser Asp Tyr Lys Leu Met
            755                 760                 765

Tyr Phe Ile Ile Glu Trp Lys Asn Leu Asn Glu Asp Gly Glu Ile Lys
        770                 775                 780

Trp Leu Arg Ile Ser Ser Val Lys Lys Tyr Tyr Ile His Asp His
785                 790                 795                 800

Phe Ile Pro Ile Glu Lys Tyr Gln Phe Ser Leu Tyr Pro Ile Phe Met
                805                 810                 815

Glu Gly Val Gly Lys Pro Lys Ile Ile Asn Ser Phe Thr Gln Asp Asp
            820                 825                 830

Ile Glu Lys His Gln Ser Asp Ala Gly Leu Tyr Val Ile Val Pro Val
        835                 840                 845

Ile Ile Ser Ser Ser Ile Leu Leu Leu Gly Thr Leu Leu Ile Ser His
        850                 855                 860

Gln Arg Met Lys Lys Leu Phe Trp Glu Asp Val Pro Asn Pro Lys Asn
865                 870                 875                 880

Cys Ser Trp Ala Gln Gly Leu Asn Phe Gln Lys Lys Met Pro Gly Thr
                885                 890                 895

Lys Glu Leu Leu Gly Gly Gly Trp Leu Thr
                900                 905

(2) INFORMATION FOR SEQ ID NO:10:

(i) SEQUENCE CHARACTERISTICS:
        (A) LENGTH: 896 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:10:

Met Ile Cys Gln Lys Phe Cys Val Val Leu Leu His Trp Glu Phe Ile
1               5                   10                  15

Tyr Val Ile Thr Ala Phe Asn Leu Ser Tyr Pro Ile Thr Pro Trp Arg
            20                  25                  30

Phe Lys Leu Ser Cys Met Pro Pro Asn Ser Thr Tyr Asp Tyr Phe Leu
        35                  40                  45

Leu Pro Ala Gly Leu Ser Lys Asn Thr Ser Asn Ser Asn Gly His Tyr
50                  55                  60

Glu Thr Ala Val Glu Pro Lys Phe Asn Ser Ser Gly Thr His Phe Ser
65                  70                  75                  80

Asn Leu Ser Lys Ala Thr Phe His Cys Cys Phe Arg Ser Glu Gln Asp
                85                  90                  95

Arg Asn Cys Ser Leu Cys Ala Asp Asn Ile Glu Gly Arg Thr Phe Val
            100                 105                 110

Ser Thr Val Asn Ser Leu Val Phe Gln Gln Ile Asp Ala Asn Trp Asn
        115                 120                 125

Ile Gln Cys Trp Leu Lys Gly Asp Leu Lys Leu Phe Ile Cys Tyr Val
        130                 135                 140

Glu Ser Leu Phe Lys Asn Leu Phe Arg Asn Tyr Asn Tyr Lys Val His
145                 150                 155                 160

Leu Leu Tyr Val Leu Pro Glu Val Leu Glu Asp Ser Pro Leu Val Pro
            165                 170                 175

Gln Lys Gly Ser Phe Gln Met Val His Cys Asn Cys Ser Val His Glu
```

```
                    180                 185                 190
Cys Cys Glu Cys Leu Val Pro Val Pro Thr Ala Lys Leu Asn Asp Thr
        195                 200                 205

Leu Leu Met Cys Leu Lys Ile Thr Ser Gly Gly Val Ile Phe Arg Ser
    210                 215                 220

Pro Leu Met Ser Val Gln Pro Ile Asn Met Val Lys Pro Asp Pro Pro
225                 230                 235                 240

Leu Gly Leu His Met Glu Thr Thr Asp Asp Gly Asn Leu Lys Ile Ser
                245                 250                 255

Trp Ser Ser Pro Pro Leu Val Pro Phe Pro Leu Gln Tyr Gln Val Lys
            260                 265                 270

Tyr Ser Glu Asn Ser Thr Thr Val Thr Arg Glu Ala Asp Lys Ile Val
        275                 280                 285

Ser Ala Thr Ser Leu Leu Val Asp Ser Ile Leu Pro Gly Ser Ser Tyr
    290                 295                 300

Glu Val Gln Val Arg Gly Lys Arg Leu Asp Gly Pro Gly Ile Trp Ser
305                 310                 315                 320

Asp Trp Ser Thr Pro Arg Val Phe Thr Thr Gln Asp Val Ile Tyr Phe
                325                 330                 335

Pro Pro Lys Ile Leu Thr Ser Val Gly Ser Asn Val Ser Phe His Cys
            340                 345                 350

Ile Tyr Lys Lys Glu Asn Lys Ile Val Pro Ser Lys Glu Ile Val Trp
        355                 360                 365

Trp Met Asn Leu Ala Glu Lys Ile Pro Gln Ser Gln Tyr Asp Val Val
    370                 375                 380

Ser Asp His Val Ser Lys Val Thr Phe Phe Asn Leu Asn Glu Thr Lys
385                 390                 395                 400

Pro Arg Gly Lys Phe Thr Tyr Asp Ala Val Tyr Cys Cys Asn Glu His
                405                 410                 415

Glu Cys His His Arg Tyr Ala Glu Leu Tyr Val Ile Asp Val Asn Ile
            420                 425                 430

Asn Ile Ser Cys Glu Thr Asp Gly Tyr Leu Thr Lys Met Thr Cys Arg
        435                 440                 445

Trp Ser Thr Ser Thr Ile Gln Ser Leu Ala Glu Ser Thr Leu Gln Leu
    450                 455                 460

Arg Tyr His Arg Ser Ser Leu Tyr Cys Ser Asp Ile Pro Ser Ile His
465                 470                 475                 480

Pro Ile Ser Glu Pro Lys Asp Cys Tyr Leu Gln Ser Asp Gly Phe Tyr
                485                 490                 495

Glu Cys Ile Phe Gln Pro Ile Phe Leu Leu Ser Gly Tyr Thr Met Trp
            500                 505                 510

Ile Arg Ile Asn His Ser Leu Gly Ser Leu Asp Ser Pro Pro Thr Cys
        515                 520                 525

Val Leu Pro Asp Ser Val Val Lys Pro Leu Pro Pro Ser Ser Val Lys
    530                 535                 540

Ala Glu Ile Thr Ile Asn Thr Gly Leu Leu Lys Ile Ser Trp Glu Lys
545                 550                 555                 560

Pro Val Phe Pro Glu Asn Asn Leu Gln Phe Gln Ile Arg Tyr Gly Leu
                565                 570                 575

Ser Gly Lys Glu Val Gln Trp Lys Met Tyr Glu Val Tyr Asp Ala Lys
            580                 585                 590

Ser Lys Ser Val Ser Leu Pro Val Pro Asp Leu Ala Cys Val Tyr Ala
        595                 600                 605
```

```
Val Gln Val Arg Cys Lys Arg Leu Asp Gly Leu Gly Tyr Trp Ser Asn
    610             615                 620

Trp Ser Asn Pro Ala Tyr Thr Val Val Met Asp Ile Lys Val Pro Met
625             630                 635                 640

Arg Gly Pro Glu Phe Trp Arg Ile Ile Asn Gly Asp Thr Met Lys Lys
                645                 650                 655

Glu Lys Asn Val Thr Leu Leu Trp Lys Pro Leu Met Lys Asn Asp Ser
            660                 665                 670

Leu Cys Ser Val Gln Arg Tyr Val Ile Asn His His Thr Ser Cys Asn
            675                 680                 685

Gly Thr Trp Ser Glu Asp Val Gly Asn His Thr Lys Phe Thr Phe Leu
            690                 695                 700

Trp Thr Glu Gln Ala His Thr Val Thr Val Leu Ala Ile Asn Ser Ile
705                 710                 715                 720

Gly Ala Ser Val Ala Asn Phe Asn Leu Thr Phe Ser Trp Pro Met Ser
                725                 730                 735

Lys Val Asn Ile Val Gln Ser Leu Ser Ala Tyr Pro Leu Asn Ser Ser
            740                 745                 750

Cys Val Ile Val Ser Trp Ile Leu Ser Pro Ser Asp Tyr Lys Leu Met
            755                 760                 765

Tyr Phe Ile Ile Glu Trp Lys Asn Leu Asn Glu Asp Gly Glu Ile Lys
770                 775                 780

Trp Leu Arg Ile Ser Ser Val Lys Lys Tyr Tyr Ile His Asp His Phe
785                 790                 795                 800

Ile Pro Ile Glu Lys Tyr Gln Phe Ser Leu Tyr Pro Ile Phe Met Glu
                805                 810                 815

Gly Val Gly Lys Pro Lys Ile Ile Asn Ser Phe Thr Gln Asp Asp Ile
            820                 825                 830

Glu Lys His Gln Ser Asp Ala Gly Leu Tyr Val Ile Val Pro Val Ile
            835                 840                 845

Ile Ser Ser Ser Ile Leu Leu Leu Gly Thr Leu Leu Ile Ser His Gln
850                 855                 860

Arg Met Lys Lys Leu Phe Trp Glu Asp Val Pro Asn Pro Lys Asn Cys
865                 870                 875                 880

Ser Trp Ala Gln Gly Leu Asn Phe Gln Lys Arg Thr Asp Ile Leu
            885                 890                 895
```

(2) INFORMATION FOR SEQ ID NO:11:

(i) SEQUENCE CHARACTERISTICS:
        (A) LENGTH: 1165 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:11:

```
Met Ile Cys Gln Lys Phe Cys Val Val Leu Leu His Trp Glu Phe Ile
1               5                   10                  15

Tyr Val Ile Thr Ala Phe Asn Leu Ser Tyr Pro Ile Thr Pro Trp Arg
            20                  25                  30

Phe Lys Leu Ser Cys Met Pro Pro Asn Ser Thr Tyr Asp Tyr Phe Leu
                35                  40                  45

Leu Pro Ala Gly Leu Ser Lys Asn Thr Ser Asn Ser Asn Gly His Tyr
        50                  55                  60

Glu Thr Ala Val Glu Pro Lys Phe Asn Ser Ser Gly Thr His Phe Ser
```

-continued

```
              65                  70                  75                  80
Asn Leu Ser Lys Thr Thr Phe His Cys Cys Phe Arg Ser Glu Gln Asp
                        85                  90                  95
Arg Asn Cys Ser Leu Cys Ala Asp Asn Ile Glu Gly Lys Thr Phe Val
                   100                 105                 110
Ser Thr Val Asn Ser Leu Val Phe Gln Gln Ile Asp Ala Asn Trp Asn
               115                 120                 125
Ile Gln Cys Trp Leu Lys Gly Asp Leu Lys Leu Phe Ile Cys Tyr Val
           130                 135                 140
Glu Ser Leu Phe Lys Asn Leu Phe Arg Asn Tyr Asn Tyr Lys Val His
145                 150                 155                 160
Leu Leu Tyr Val Leu Pro Glu Val Leu Glu Asp Ser Pro Leu Val Pro
                   165                 170                 175
Gln Lys Gly Ser Phe Gln Met Val His Cys Asn Cys Ser Val His Glu
               180                 185                 190
Cys Cys Glu Cys Leu Val Pro Val Pro Thr Ala Lys Leu Asn Asp Thr
           195                 200                 205
Leu Leu Met Cys Leu Lys Ile Thr Ser Gly Val Ile Phe Gln Ser
210                 215                 220
Pro Leu Met Ser Val Gln Pro Ile Asn Met Val Lys Pro Asp Pro Pro
225                 230                 235                 240
Leu Gly Leu His Met Glu Thr Thr Asp Asp Gly Asn Leu Lys Ile Ser
                   245                 250                 255
Trp Ser Ser Pro Pro Leu Val Pro Phe Pro Leu Gln Tyr Gln Val Lys
               260                 265                 270
Tyr Ser Glu Asn Ser Thr Thr Val Thr Arg Glu Ala Asp Lys Ile Val
           275                 280                 285
Ser Ala Thr Ser Leu Leu Val Asp Ser Ile Leu Pro Gly Ser Ser Tyr
       290                 295                 300
Glu Val Gln Val Arg Gly Lys Arg Leu Asp Gly Pro Gly Ile Trp Ser
305                 310                 315                 320
Asp Trp Ser Thr Pro Arg Val Phe Thr Thr Gln Asp Val Ile Tyr Phe
                   325                 330                 335
Pro Pro Lys Ile Leu Thr Ser Val Gly Ser Asn Val Ser Phe His Cys
               340                 345                 350
Ile Tyr Lys Lys Glu Asn Lys Ile Val Pro Ser Lys Glu Ile Val Trp
           355                 360                 365
Trp Met Asn Leu Ala Glu Lys Ile Pro Gln Ser Gln Tyr Asp Val Val
       370                 375                 380
Ser Asp His Val Ser Lys Val Thr Phe Phe Asn Leu Asn Glu Thr Lys
385                 390                 395                 400
Pro Arg Gly Lys Phe Thr Tyr Asp Ala Val Tyr Cys Cys Asn Glu His
                   405                 410                 415
Glu Cys His His Arg Tyr Ala Glu Leu Tyr Val Ile Asp Val Asn Ile
               420                 425                 430
Asn Ile Ser Cys Glu Thr Asp Gly Tyr Leu Thr Lys Met Thr Cys Arg
           435                 440                 445
Trp Ser Thr Ser Thr Ile Gln Ser Leu Ala Glu Ser Thr Leu Gln Leu
       450                 455                 460
Arg Tyr His Arg Ser Ser Leu Tyr Cys Ser Asp Ile Pro Ser Ile His
465                 470                 475                 480
Pro Ile Ser Glu Pro Lys Asp Cys Tyr Leu Gln Ser Asp Gly Phe Tyr
                   485                 490                 495
```

-continued

```
Glu Cys Ile Phe Gln Pro Ile Phe Leu Leu Ser Gly Tyr Thr Met Trp
            500                 505                 510

Ile Arg Ile Asn His Ser Leu Gly Ser Leu Asp Ser Pro Thr Cys
        515                 520                 525

Val Leu Pro Asp Ser Val Val Lys Pro Leu Pro Ser Ser Val Lys
530                 535                 540

Ala Glu Ile Thr Ile Asn Thr Gly Leu Leu Lys Ile Ser Trp Glu Lys
545                 550                 555                 560

Pro Val Phe Pro Glu Asn Asn Leu Gln Phe Gln Ile Arg Tyr Gly Leu
                565                 570                 575

Ser Gly Lys Glu Val Gln Trp Lys Met Tyr Glu Val Tyr Asp Ala Lys
            580                 585                 590

Ser Lys Ser Val Ser Leu Pro Val Pro Asp Leu Ala Cys Val Tyr Ala
        595                 600                 605

Val Gln Val Arg Cys Lys Arg Leu Asp Gly Leu Gly Tyr Trp Ser Asn
610                 615                 620

Trp Ser Asn Pro Ala Tyr Thr Val Val Met Asp Ile Lys Val Pro Met
625                 630                 635                 640

Arg Gly Pro Glu Phe Trp Arg Ile Ile Asn Gly Asp Thr Met Lys Lys
                645                 650                 655

Glu Lys Asn Val Thr Leu Leu Trp Lys Pro Leu Met Lys Asn Asp Ser
            660                 665                 670

Leu Cys Ser Val Gln Arg Tyr Val Ile Asn His His Thr Ser Cys Asn
        675                 680                 685

Gly Thr Trp Ser Glu Asp Val Gly Asn His Thr Lys Phe Thr Phe Leu
690                 695                 700

Trp Thr Glu Gln Ala His Thr Val Thr Val Leu Ala Ile Asn Ser Ile
705                 710                 715                 720

Gly Ala Ser Val Ala Asn Phe Asn Leu Thr Phe Ser Trp Pro Met Ser
                725                 730                 735

Lys Val Asn Ile Val Gln Ser Leu Ser Ala Tyr Pro Leu Asn Ser Ser
            740                 745                 750

Cys Val Ile Val Ser Trp Ile Leu Ser Pro Ser Asp Tyr Lys Leu Met
        755                 760                 765

Tyr Phe Ile Ile Glu Trp Lys Asn Leu Asn Glu Asp Gly Glu Ile Lys
770                 775                 780

Trp Leu Arg Ile Ser Ser Ser Val Lys Lys Tyr Tyr Ile His Asp His
785                 790                 795                 800

Phe Ile Pro Ile Glu Lys Tyr Gln Phe Ser Leu Tyr Pro Ile Phe Met
                805                 810                 815

Glu Gly Val Gly Lys Pro Lys Ile Ile Asn Ser Phe Thr Gln Asp Asp
            820                 825                 830

Ile Glu Lys His Gln Ser Asp Ala Gly Leu Tyr Val Ile Val Pro Val
        835                 840                 845

Ile Ile Ser Ser Ser Ile Leu Leu Leu Gly Thr Leu Leu Ile Ser His
850                 855                 860

Gln Arg Met Lys Lys Leu Phe Trp Glu Asp Val Pro Asn Pro Lys Asn
865                 870                 875                 880

Cys Ser Trp Ala Gln Gly Leu Asn Phe Gln Lys Pro Glu Thr Phe Glu
                885                 890                 895

His Leu Phe Ile Lys His Thr Ala Ser Val Thr Cys Gly Pro Leu Leu
            900                 905                 910

Leu Glu Pro Glu Thr Ile Ser Glu Asp Ile Ser Val Asp Thr Ser Trp
        915                 920                 925
```

-continued

```
Lys Asn Lys Asp Glu Met Met Pro Thr Thr Val Val Ser Leu Leu Ser
            930                 935                 940

Thr Thr Asp Leu Glu Lys Gly Ser Val Cys Ile Ser Asp Gln Phe Asn
945                 950                 955                 960

Ser Val Asn Phe Ser Glu Ala Glu Gly Thr Glu Val Thr Tyr Glu Ala
                965                 970                 975

Glu Ser Gln Arg Gln Pro Phe Val Lys Tyr Ala Thr Leu Ile Ser Asn
            980                 985                 990

Ser Lys Pro Ser Glu Thr Gly Glu Gln Glu Leu Ile Asn Ser Ser
            995                 1000                1005

Val Thr Lys Cys Phe Ser Ser Lys Asn Ser Pro Leu Lys Asp Ser Phe
    1010                1015                1020

Ser Asn Ser Ser Trp Glu Ile Glu Ala Gln Ala Phe Phe Ile Leu Ser
1025                1030                1035                1040

Asp Gln His Pro Asn Ile Ile Ser Pro His Leu Thr Phe Ser Glu Gly
                1045                1050                1055

Leu Asp Glu Leu Leu Lys Leu Glu Gly Asn Phe Pro Glu Glu Asn Asn
            1060                1065                1070

Asp Lys Lys Ser Ile Tyr Tyr Leu Gly Val Thr Ser Ile Lys Lys Arg
            1075                1080                1085

Glu Ser Gly Val Leu Leu Thr Asp Lys Ser Arg Val Ser Cys Pro Phe
            1090                1095                1100

Pro Ala Pro Cys Leu Phe Thr Asp Ile Arg Val Leu Gln Arg Ser Cys
1105                1110                1115                1120

Ser His Phe Val Gln Asn Asn Ile Asn Leu Gly Thr Ser Ser Lys Lys
                1125                1130                1135

Thr Phe Ala Ser Tyr Met Pro Gln Phe Gln Thr Cys Ser Thr Gln Thr
                1140                1145                1150

Thr His Lys Ile Met Glu Lys Met Cys Asp Leu Thr Val
                1155                1160                1165

(2) INFORMATION FOR SEQ ID NO:12:

(i) SEQUENCE CHARACTERISTICS:
        (A) LENGTH: 896 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:12:

Met Met Cys Gln Lys Phe Tyr Val Val Leu Leu His Trp Glu Phe Leu
1               5                   10                  15

Tyr Val Ile Thr Ala Leu Asn Leu Ala Tyr Pro Ile Ser Pro Trp Lys
                20                  25                  30

Phe Lys Leu Phe Cys Gly Pro Pro Asn Thr Thr Asp Asp Ser Phe Leu
                35                  40                  45

Ser Pro Ala Gly Ala Pro Asn Asn Ala Ser Ala Leu Lys Gly Ala Ser
            50                  55                  60

Glu Ala Ile Val Glu Pro Lys Phe Asn Ser Ser Glu Ile Tyr Val Pro
65                  70                  75                  80

Asn Leu Ser Lys Ser Glu Phe His Cys Cys Phe Glu Asn Glu Gln Glu
                85                  90                  95

Gln Asn Cys Ser Ala Leu Thr Asp Asn Thr Glu Gly Lys Thr Leu Ala
            100                 105                 110
```

-continued

```
Ser Val Val Lys Ala Ser Val Phe Arg Gln Leu Gly Val Asn Trp Asp
            115                 120                 125
Ile Glu Cys Trp Met Lys Gly Asp Leu Lys Thr Phe Ile Cys His Met
130                 135                 140
Glu Pro Leu Pro Lys Asn Pro Phe Lys Asn Tyr Asp Ser Lys Val His
145                 150                 155                 160
Leu Leu Tyr Asp Leu Pro Glu Val Ile Asp Ser Pro Leu Pro Pro
                165                 170                 175
Leu Lys Asp Ser Phe Gln Thr Val Gln Cys Asn Cys Ser Leu Arg Gly
                180                 185                 190
Cys Xaa Glu Cys His Val Pro Val Pro Arg Ala Lys Leu Asn Tyr Ala
            195                 200                 205
Leu Leu Met Tyr Leu Glu Ile Thr Ser Ala Gly Val Ser Phe Gln Ser
210                 215                 220
Pro Leu Met Ser Leu Gln Pro Met Leu Val Val Lys Pro Asp Pro Pro
225                 230                 235                 240
Leu Gly Leu His Met Glu Val Thr Asp Asp Gly Asn Leu Lys Ile Ser
                245                 250                 255
Trp Asp Ser Gln Thr Met Ala Pro Phe Pro Leu Gln Tyr Gln Val Lys
            260                 265                 270
Tyr Leu Glu Asn Ser Thr Ile Val Arg Glu Ala Ala Xaa Glu Ile Val
            275                 280                 285
Ser Ala Thr Ser Leu Leu Val Asp Ser Val Leu Pro Gly Ser Ser Tyr
290                 295                 300
Glu Val Gln Val Arg Ser Lys Arg Leu Asp Gly Ser Gly Val Trp Ser
305                 310                 315                 320
Asp Trp Ser Ser Pro Gln Val Phe Thr Thr Gln Asp Val Val Tyr Phe
                325                 330                 335
Pro Pro Lys Ile Leu Thr Ser Val Gly Ser Asn Ala Ser Phe His Cys
                340                 345                 350
Ile Tyr Lys Asn Glu Asn Gln Ile Ile Ser Ser Lys Gln Ile Val Trp
            355                 360                 365
Trp Met Asn Leu Ala Glu Lys Ile Pro Glu Ile Gln Tyr Ser Ile Val
            370                 375                 380
Ser Asp Arg Val Ser Lys Val Thr Phe Ser Asn Leu Lys Ala Thr Arg
385                 390                 395                 400
Pro Arg Gly Lys Phe Thr Tyr Asp Ala Val Tyr Cys Cys Asn Glu Gln
                405                 410                 415
Ala Cys His His Arg Tyr Ala Glu Leu Tyr Val Ile Asp Val Asn Ile
                420                 425                 430
Asn Ile Ser Cys Glu Thr Asp Gly Tyr Leu Thr Lys Met Thr Cys Arg
            435                 440                 445
Trp Ser Pro Ser Thr Ile Gln Ser Leu Val Gly Ser Thr Val Gln Leu
450                 455                 460
Arg Tyr His Arg Arg Ser Leu Tyr Cys Pro Asp Ser Pro Ser Ile His
465                 470                 475                 480
Pro Thr Ser Glu Pro Lys Asn Cys Val Leu Gln Arg Asp Gly Phe Tyr
                485                 490                 495
Glu Cys Val Phe Gln Pro Ile Phe Leu Leu Ser Gly Tyr Thr Met Trp
                500                 505                 510
Ile Arg Ile Asn His Ser Leu Gly Ser Leu Asp Ser Pro Pro Thr Cys
            515                 520                 525
Val Leu Pro Asp Ser Val Val Lys Pro Leu Pro Pro Ser Asn Val Lys
530                 535                 540
```

```
Ala Glu Ile Thr Val Asn Thr Gly Leu Leu Lys Val Ser Trp Glu Lys
545                 550                 555                 560

Pro Val Phe Pro Glu Asn Asn Leu Gln Phe Gln Ile Arg Tyr Gly Leu
                565                 570                 575

Ser Gly Lys Glu Ile Gln Trp Lys Thr His Glu Val Tyr Asp Ala Lys
                580                 585                 590

Ser Lys Ser Ala Ser Leu Leu Val Ser Asp Leu Ala Cys Val Tyr Val
        595                 600                 605

Val Gln Val Arg Cys Arg Arg Leu Asp Gly Leu Gly Tyr Trp Ser Asn
    610                 615                 620

Trp Ser Ser Pro Ala Tyr Thr Leu Val Met Asp Val Lys Val Pro Met
625                 630                 635                 640

Arg Gly Pro Glu Phe Trp Arg Ile Met Asp Gly Asp Val Thr Lys Lys
                645                 650                 655

Glu Arg Asn Val Thr Leu Leu Trp Lys Pro Leu Thr Lys Asn Asp Ser
                660                 665                 670

Leu Cys Ser Val Arg Arg Tyr Val Val Lys His Arg Thr Ala His Asn
        675                 680                 685

Gly Thr Trp Ser Glu Asp Val Glu Asn Arg Thr Lys Leu Thr Phe Leu
    690                 695                 700

Trp Thr Glu Pro Ala His Thr Val Thr Val Leu Ala Val Asn Ser Leu
705                 710                 715                 720

Gly Ala Ser Leu Val Asn Phe Asn Leu Thr Phe Ser Trp Pro Met Ser
                725                 730                 735

Lys Val Ser Ala Val Glu Ser Leu Ser Ala Tyr Pro Leu Ser Ser Ser
                740                 745                 750

Cys Val Ile Leu Ser Trp Thr Leu Ser Pro Asp Asp Tyr Ser Leu Leu
        755                 760                 765

Tyr Leu Val Ile Glu Trp Lys Ile Leu Asn Glu Asp Asp Gly Met Lys
    770                 775                 780

Trp Leu Arg Ile Pro Ser Asn Val Lys Lys Phe Tyr Ile His Asp Asn
785                 790                 795                 800

Phe Ile Pro Ile Glu Lys Tyr Gln Phe Ser Leu Tyr Pro Val Phe Met
                805                 810                 815

Glu Gly Val Gly Lys Pro Lys Ile Ile Asn Gly Phe Thr Lys Asp Ala
                820                 825                 830

Ile Asp Lys Gln Gln Asn Asp Ala Gly Leu Tyr Val Ile Val Pro Ile
        835                 840                 845

Ile Ile Ser Ser Cys Val Leu Leu Leu Gly Thr Leu Leu Ile Ser His
    850                 855                 860

Gln Arg Met Lys Lys Leu Phe Trp Asp Asp Val Pro Asn Pro Lys Asn
865                 870                 875                 880

Cys Ser Trp Ala Gln Gly Leu Asn Phe Gln Lys Arg Thr Asp Thr Leu
                885                 890                 895
```

(2) INFORMATION FOR SEQ ID NO:13:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

```
GGTTTGCATA TGGAAGTC                                                      18

(2) INFORMATION FOR SEQ ID NO:14:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

CCTGAACCAT CCAGTCTCT                                                     19

(2) INFORMATION FOR SEQ ID NO:15:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:15:

GACTCATTGT GCAGTGTTCA G                                                  21

(2) INFORMATION FOR SEQ ID NO:16:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:16:

TAGTGGAGGG AGGGTCAGCA G                                                  21
```